United States Patent
Maki et al.

(10) Patent No.: US 7,440,794 B2
(45) Date of Patent: Oct. 21, 2008

(54) OPTICAL SYSTEM FOR MEASURING METABOLISM IN A BODY AND IMAGING METHOD

(75) Inventors: Atsushi Maki, Hachioji (JP); Hideaki Koizumi, Tokyo (JP); Fumio Kawaguchi, Tokyo (JP); Yuichi Yamashita, Kawagoe (JP); Yoshitoshi Ito, Ome (JP)

(73) Assignee: Hitachi, Ltd., Tokyo (JP)

( * ) Notice: Subject to any disclaimer, the term of this patent is extended or adjusted under 35 U.S.C. 154(b) by 480 days.

(21) Appl. No.: 11/037,282

(22) Filed: Jan. 19, 2005

(65) Prior Publication Data
US 2005/0148857 A1 Jul. 7, 2005

Related U.S. Application Data

(63) Continuation of application No. 09/900,144, filed on Jul. 9, 2001, now Pat. No. 7,286,870, which is a continuation of application No. 09/203,610, filed on Dec. 2, 1998, now Pat. No. 6,282,438, which is a continuation of application No. 09/149,155, filed on Sep. 8, 1998, now Pat. No. 6,128,517, which is a continuation of application No. 08/539,871, filed on Oct. 6, 1995, now Pat. No. 5,803,909.

(30) Foreign Application Priority Data

| Oct. 6, 1994 | (JP) | 06-242592 |
| Feb. 20, 1995 | (JP) | 07-030972 |
| Jul. 5, 1995 | (JP) | 07-169820 |

(51) Int. Cl.
*A61B 5/00* (2006.01)
(52) U.S. Cl. .................................... 600/473
(58) Field of Classification Search ............... 600/476, 600/473, 334, 310, 407, 479, 409; 356/41
See application file for complete search history.

(56) References Cited

U.S. PATENT DOCUMENTS 4,170,987 A 10/1979 Anselmo et al.

(Continued)

FOREIGN PATENT DOCUMENTS

EP 0497021 9/1992

(Continued)

OTHER PUBLICATIONS

M. Dujovny et al., "Intercerebral penetration of infrared light," *J. Neurosurg.*, Feb. 1992.

(Continued)

*Primary Examiner*—Eric F Winakur
*Assistant Examiner*—Lawrence N Laryea
(74) *Attorney, Agent, or Firm*—Antonelli, Terry, Stout & Kraus, LLP.

(57) ABSTRACT

In an optical measurement system and imaging method adapted to measure in vivo information in a living body without harming the living body, light rays of a plurality of wavelengths which are modulated in intensity with a plurality of different frequencies are irradiated on a plurality of irradiation positions on the surface of a living body, and time-variable changes in living body transmitting light intensity levels corresponding to the respective wavelengths and the respective irradiation positions are measured at different positions on the surface of the living body. Light is utilized to image the results of the measurements, in which the measuring time is shortened by estimating fluctuation attributable to the living body, and the presence or absence of a change in measured signal can be decided easily by displaying an estimation signal and a measured signal at a time.

20 Claims, 21 Drawing Sheets

U.S. PATENT DOCUMENTS

| | | | |
|---|---|---|---|
| 4,223,680 A | 9/1980 | Jöbsis | |
| 4,281,645 A | 8/1981 | Jobsis | |
| 4,515,165 A | 5/1985 | Carroll | |
| 4,736,751 A | 4/1988 | Gevins et al. | |
| 5,088,493 A | 2/1992 | Giannini et al. | |
| 5,090,415 A | 2/1992 | Yamashita et al. | |
| 5,103,829 A * | 4/1992 | Suzuki et al. | 600/310 |
| 5,122,974 A | 6/1992 | Chance | |
| 5,137,355 A | 8/1992 | Barbour et al. | |
| 5,198,977 A | 3/1993 | Salb | |
| 5,215,095 A | 6/1993 | Macvicar et al. | |
| 5,271,401 A * | 12/1993 | Fishman | 424/9.4 |
| 5,291,888 A | 3/1994 | Tucker | |
| 5,321,265 A | 6/1994 | Block | |
| 5,396,571 A | 3/1995 | Saadatmanesh et al. | |
| 5,419,320 A | 5/1995 | Kawaguchi et al. | |
| 5,438,989 A | 8/1995 | Hochman et al. | |
| 5,465,718 A | 11/1995 | Hochman et al. | |
| 5,517,987 A | 5/1996 | Tsuchiya | |
| 5,551,422 A * | 9/1996 | Simonsen et al. | 600/322 |
| 5,566,673 A | 10/1996 | Shiono et al. | |
| 5,586,554 A | 12/1996 | Maki et al. | |
| 5,678,556 A | 10/1997 | Maki et al. | |
| 5,772,597 A | 6/1998 | Goldberger et al. | |
| 5,803,909 A | 9/1998 | Maki et al. | |
| 5,954,053 A | 9/1999 | Chance et al. | |
| 6,128,517 A | 10/2000 | Maki et al. | |
| 6,196,226 B1 | 3/2001 | Hochman et al. | |
| 6,210,346 B1 | 4/2001 | Hall et al. | |
| 6,233,480 B1 | 5/2001 | Hochman et al. | |
| 6,282,438 B1 | 8/2001 | Maki et al. | |
| 6,542,763 B1 | 4/2003 | Yamashita et al. | |
| 6,611,698 B1 | 8/2003 | Yamashita et al. | |

FOREIGN PATENT DOCUMENTS

| | | |
|---|---|---|
| JP | 55-024004 | 2/1980 |
| JP | 57-115232 | 7/1982 |
| JP | 60-72542 | 4/1985 |
| JP | 60-072542 | 4/1985 |
| JP | 62-231625 | 10/1987 |
| JP | 63-277038 | 11/1988 |
| JP | 64-46439 | 2/1989 |
| JP | 64-046439 | 2/1989 |
| JP | 2-066429 | 3/1990 |
| JP | 2-203250 | 8/1990 |
| JP | 2-303250 | 8/1990 |
| JP | 3-67409 | 3/1991 |
| JP | 3-505922 | 12/1991 |
| JP | 4-502118 | 4/1992 |
| JP | 5-103773 | 4/1993 |
| JP | 5-103774 | 4/1993 |
| JP | 5-103837 | 4/1993 |
| JP | 5-86304 | 11/1993 |
| JP | 5-300887 | 11/1993 |
| JP | 6-14908 | 1/1994 |
| JP | 6-090933 | 4/1994 |
| JP | 6-154228 | 6/1994 |
| JP | 6-245938 | 6/1994 |
| JP | 7-49304 | 2/1995 |
| JP | 7-49307 | 2/1995 |
| JP | 7-079935 | 3/1995 |
| JP | 7-113743 | 5/1995 |
| JP | 7-120384 | 5/1995 |
| JP | 7-128231 | 5/1995 |
| JP | 7-148169 | 6/1995 |
| JP | 7-507472 | 8/1995 |
| WO | 93/25141 | 12/1993 |
| WO | 93/25145 | 12/1993 |
| WO | 94/10901 | 5/1994 |

OTHER PUBLICATIONS

S. Feng et al., "Monte Carlo simulations of photon migration path distributions in multiple scattering media," SPIE, vol. 1888, pp. 78-89.

Gopinath et al., "Near-infrared spectroscopic localization of intracranial hemotomas," *J. Neurosurg.*, 79:43-47, 1993.

Chance, et al., Cognition-activated low-frequency modulation of light absorption in human brain, Proc. Natl. Acad. Sci. USA 90, pp. 3770-3774 (1993).

Kwan, et al., Human cortical erfusion and the arterial pulse: a near-infrared spectroscopy study, 2004.

* cited by examiner

OPTICAL SYSTEM FOR MEASURING METABOLISM IN A BODY AND IMAGING METHOD

CROSS-REFERENCE TO RELATED APPLICATIONS

This is a continuation of application Ser. No. 09/900,144 filed 9 Jul. 2001, now U.S. Pat. No. 7,286,870, which is a continuation of application Ser. No. 09/203,610 filed 2 Dec. 1998, now U.S. Pat. No. 6,282,438 B1, which is a continuation of application Ser. No. 09/149,155 filed 8 Sep. 1998, now U.S. Pat. No. 6,128,517 A, which is a continuation of application Ser. No. 08/539,871 filed 6 Oct. 1995, now U.S. Pat. No. 5,803,909 A, the disclosures of all of which are incorporated herein by reference in their entirety.

BACKGROUND OF THE INVENTION

The present invention relates to a living body optical measurement system and an imaging method in the system and more particularly, to a living body optical measurement system and an imaging method which are adapted to measure in vivo information by using light and to image results of measurement.

Desired in clinical medical treatment is a system or a method for measuring the interior of a living body with ease without adversely affecting the living body. Measurement using light is very effective to the desirability. The first reason for this is that the oxygen metabolic function inside the living body corresponds to the concentration of a specified pigment (hemoglobin, cytochrome aa3, myoglobin or the like) in the living body, that is, the concentration of a light absorber and the concentration of the specified pigment can be determined from an absorption amount for light (having wavelengths of from visible rays to near infrared rays). The second reason is that light can be handled easily by optical fibers. The third reason is that optical measurement does not harm the living body when used within the safety standards.

A system which utilizes the advantages of the living body measurement based on light to irradiate light having wavelengths of from visible rays to near infrared rays on a living body and measure the interior of the living body from reflection light at a location about 10 to 50 mm distant from an irradiation position is described in, for example, patent disclosures of JP-A-63-277038 and JP-A-5-300887. Also, a system for measuring CT images of the oxygen metabolic function from light transmitting through a living body having a thickness of 100 to 200 mm, that is, an optical CT system is described in, for example, patent disclosures of JP-A-60-72542 and JP-A-62-231625.

Known as a conventional living body optical measurement system is an oximeter for measuring the degree of oxygen saturation in the artery (JP-A-55-24004). The oximeter is a system in which light having a plurality of wavelengths is irradiated on a living body, the transmitting light intensity or reflection light intensity from the living body is measured, and spectroscopic characteristics of reduced hemoglobin (Hb) and hemoglobin oxide (HbO2) and pulsation waves are utilized to calculate the degree of oxygen saturation in the artery.

Also known as a method for measuring the degree of oxygen saturation in tissues of a living body (average degree of oxygen saturation in both the artery system and the vein system) and the hemodynamic amount is a method by Jöbsus et al (JP-A-57-115232). This method utilizes spectroscopic characteristics of Hb and HbO2 to measure the degree of oxygen saturation and the hemodynamic amount in tissues of a living body.

To add, in the present specification, transmitting light, reflection light and scattering light are not particularly discriminated from each other and the intensity of light which is emitted from a light source, interacts with a living body and then is detected by a photodetector is called the transmitting light intensity.

Problems that the invention is to solve are three as below.
(First Problem)

In order to analyze the function of a living body, a change in hemodynamic movement due to loading is sometimes measured from the difference between the hemodynamic movement when a load is applied to the living body and the change in hemodynamic movement during unloading.

The hemodynamic movement during unloading is not always constant but changes with time. As an example, a time-variable change in transmitting light intensity is shown in FIG. 1 which is obtained when light is irradiated on a temporal of a subject who lies quietly on his or her back and the transmitting light intensity is measured at a point 3 cm distant from a light irradiation position. As illustrated in FIG. 1, while fluctuation in the measuring system is only about 0.3%, the living body transmitting light intensity changes irregularly and greatly as a whole while exhibiting periodical change components. The fluctuation in transmitting light intensity is attributable to a change in the hemodynamic movement in the living body.

Even when the subject keeps quiet, the irregular change occurs in the transmitting light intensity signal in this manner and consequently, when the transmitting light intensity upon start of measurement is treated as a reference value, change in hemodynamic movement due to load is difficult to separate from the measured signal. Further, this causes the observer to be prevented from deciding whether a time-variable change in a measured signal displayed on a display unit or a time-variable change in hemodynamic movement calculated from the measured signal is due to fluctuation owned by the living body or is due to the application of a load. Accordingly, in the prior arts, the transmitting light intensity upon start of measurement is treated as the reference value and therefore, there arises a problem that the subject must be kept to be quiet to maintain the reference value and the measurement cannot be proceeded with for a long period of time until the signal becomes stable.

(Second Problem)

It has hitherto been known to optically measure the cerebral cortex under the skull with an optical spot by means of a light generating and receiving element and a fiber, but measurement of an image of a hemodynamic state covered with the protective tissues such as skin tissues and bone tissues, that is, measurement with a plurality of measuring points, has been neither disclosed nor suggested. For example, when oxygen metabolism changes locally, it has been difficult to detect where the change occurs.

For extraction of light signals, the measuring time, i.e., the number of integral operations of measurement must be increased. As a result, the measuring time is prolonged and not only a mental burden is imposed on the subject but also the operation efficiency of the system is degraded.

The present invention intends to solve the prior art problems as above.

(Third Problem)

With the prior arts, the degree of oxygen saturation in the artery or the hemodynamic movement in the living body tissues can be measured. But, the prior arts cannot discriminate an change in hemodynamic movement due to an overall change in the living body from a change in hemodynamic movement due to a local change in the living body.

On the other hand, only the change in hemodynamic movement due to the local change in the living body is sometimes desired to be detected.

For example, in the cerebrum of the living body, a local portion exists which acts in correspondence to each function of the living body (hereinafter referred to as a functional portion) and the hemodynamic amount or the degree of oxygen saturation at the functional portion of the cerebrum changes locally in correspondence to an arbitrary function of the living body. At that time, if a change in hemodynamic amount or in degree of oxygen saturation at only the arbitrary functional portion can be measured locally, then the action of the cerebral functional portion can be examined in detail, contributing to a great importance from the standpoint of medical science.

For example, the signal representative of fluctuation in transmitting light intensity in FIG. 1 is difficult to discriminate because an overall hemodynamic movement signal in the living body is accompanied by fluctuation and even when only the local hemodynamic movement changes, a signal indicative of the change is buried in the fluctuation.

SUMMARY OF THE INVENTION

An object of the present invention is to solve the above problems and to realize a living body optical measurement system which images a state of a function of the living body by using simplified detectors through measurement within a short period of time and a method for imaging results of measurement by using the system.

Another object of the present invention is to perform measurement which is difficult to achieve with the prior arts and in which a local change in hemodynamic movement is measured separately and discriminatively from an overall change in hemodynamic movement in the living body.

(For the First Problem)

When a change in hemodynamic movement due to load is measured, measurement is carried out by alternately providing time during which the load is not applied to a living body (unloading time) and time during which the load is applied to the living body (loading time). Here, where a signal measured by the living body optical measurement system (measured signal) is Sm(t), a signal due to a change in hemodynamic movement during unloading (non-load signal) is Str(t), and a signal due to a change in hemodynamic movement during loading (load signal) is Sl(t), the measured signal Sm(t) is given by the following equation (1):

$$Sm(t)=Str(t)+Sl(t) \quad (1),$$

t being the measuring time.

In the present invention, a signal during the non-load time is extracted from the measured signal Sm(t) to predict the function Str(t) indicative of the non-load signal (estimated non-load signal) and the load signal Sl(t) is determined from the difference between the measured signal Sm(t) and the estimated non-load signal Str(t). Further, by displaying the determined measured signal and the predicted non-load signal at a time, thus making it easy to decide whether fluctuation in the measured signal is due to fluctuation in the load or due to fluctuation attributable to the living body during unloading.

Determination of the function Str(t) can be effected by inputting an arbitrary function having indefinite coefficients into a computer through, for example, a keyboard and determining the indefinite coefficients by, for example, the method of least squares such that the function fits optimally to the non-load signal. The load signal Sl(t) does not fall to zero as soon as the load is removed from the living body and therefore, by setting the predetermined relaxation time following the loading time and determining the function Str(t) by using the measuring time corresponding to the unloading time exclusive of the relaxation time, a more accurate function Str(t) can be determined.

The above function Str(t) can be determined such that a single function can cover a plurality of load times, for example, the entire measuring time or can be determined every load time so as to cover only the respective load times. With a method of determining functions St(t) for the respective load times by using measured signals Sm(t) obtained before and after each load time, high estimated accuracy can be obtained.

(For the Second Problem)

To achieve the above object, a living body optical measurement system according to the present invention comprises a plurality of light irradiation units for irradiating light rays having the wavelength range of from visible rays to near infrared rays on a subject, a plurality of light receiving units for detecting light rays irradiated from the light irradiation units and transmitting through the interior of the subject, a memory for storing, in time sequence, signals detected by the light receiving units and delivered out of the respective ones of the plurality of light receiving units, an arithmetic unit for performing conversion into signals of measured objects at a plurality of measuring points by using the signals stored in the memory, and an image preparation unit for determining a signal at a measuring position from the output of the arithmetic unit is measured presumptively and displaying the determined signal as an image indicative of an intensity signal on a two-dimensional display screen. In particular, each of the plurality of light irradiation units includes a plurality of light sources having different wavelengths, modulators for modulating the light rays of the plurality of light sources with different frequencies, and wave guides for guiding a plurality of modulated light rays to the irradiation positions, and each of the plurality of light receiving units includes a splitter for splitting the intensity of light from each of the plurality of light sources having the different wavelengths.

The presumptive measuring position location is intermediate between the light irradiation unit and the light receiving unit and more specifically, the exact presumptive measuring position is an intermediate portion between a living body surface position irradiated with the light form the light irradiation unit and a light receiving surface position of the living body. Here, however, the light irradiation unit is close to the light receiving unit and therefore, it is not particularly problematic that the presumptive measuring position can be replaced with substantial half the distance between the center of the light irradiation unit and the light receiving unit. Further, in one method for determination of the intermediate position, light from the light irradiation unit is irradiated on the living body and signals are detected by two light receiving units disposed at sites which are symmetrical to the light irradiation unit. The difference signal between these signals is produced and an intermediate location between the light receiving unit location and the light irradiation unit which is obtained by positioning the light receiving units through such an adjustment of the two light receiving units that the difference signal is rendered to be zero level.

To make up the above description, when the function of the interior of a living body is measured using the above living body optical measurement system, light irradiation positions of the plurality of light irradiation means are distributively arranged on a measuring portion of a subject, a plurality of light receiving portions of the plurality of light receiving means are disposed around the distributively arranged light irradiation positions, respectively, and for light signals detected by the plurality of light receiving means, a position on a perpendicular vertical to the living body surface, which position is an intermediate point between the light irradiation position and the light detection position and extending to the interior of the living body is set as a presumptive measuring point. The signal at the presumptive measuring point is calculated by the light signal detected by the plural light receiving means. This is because according to spatial characteristics of light density irradiated from the light irradiation position and then reaching the detection position, the density is high immediately below the irradiation position and the detection position near the surface by virtue of scattering of light from the surface but when an arbitrary depth determined by the distance between light irradiation position and detection position and the light scattering characteristics of the living body is exceeded, the density becomes the highest even at an intermediate location between the irradiation position and the detection position and eventually, the sensitivity becomes the highest at the intermediate location. Light signal intensity detected in correspondence to the aforementioned presumptive measuring point and measuring point is displayed on a two-dimensional image. When the light signal intensity is desired to be displayed as a topography image, signals at unmeasured locations can be obtained in the form of interpolated signals associated with the aforementioned presumptive measuring points.

When the above subject is a living body, the distance between the irradiation position and the detection position is preferably 10 to 50 mm. Here, determination of the factor for determining the maximum distance has relation to the intensity of irradiated light and attenuation in the living body.

(For the Third Problem)

Advantageously, in the present invention, light rays are irradiated from a desired single site or a plurality of sites on a living body, two sites of a detection position at which a local change is measured as a change in signal and a detection position at which a local change is not measured as a change in signal are set to be substantially equidistant from a light irradiation position, transmitting light intensity levels are detected at the respective detection positions, and the difference between transmitting light intensity levels at the two sites is produced, so that a fluctuation component in the living body common to the two detection positions can be removed to permit a slight change in one of the light receiving units to be detected with high sensitivity. When the aforementioned two sites of detection position cannot be found, the light irradiation position is displaced to find the detection positions. Namely, like a stethoscope, wanted measuring positions can be searched.

Preferably, transmitting light rays are received at two sites of detection positions equidistant from the incident position and differently positioned, transmitting light intensity levels at the respective detection positions are converted into electric signals by using photoelectric conversion elements such as photodiodes or photomultiplier tubes (hereinafter, electric signals meaning the transmitting light intensities will be referred to as transmitting light intensity signals), the individual transmitting light signal intensity levels are subjected to logarithmic conversion by means of logarithmic amplifiers, and a transmitting light intensity signal at the first detection position and a transmitting light intensity signal at the second detection position are then amplified and detected by differential amplifiers.

By modulating light emitted from the light source in intensity and extracting only a frequency component for intensity modulation of a detected signal, noises due to external disturbance can be removed.

The light source can be connected to the light irradiation position through an optical fiber and the light detection position can be connected to the photodetector through an optical fiber.

Since, in the present invention, information about a measuring position can be determined substantially definitely by the position at which light is irradiated on a subject by the light irradiation means and the position of the light receiving means, the signal processing for displaying the information as an image can be conducted easily at a high speed. Also, with the light receiving means disposed about 10 to 50 mm closely to the light irradiation position, transmitting light is utilized to obtain the detection intensity which is sufficiently high, amounting to about 6 order or more higher than light transmitting through a living body of about 100 to 200 mm. Therefore, measurement can be carried out with simplified photodetectors and can be completed within a short period of time.

For example, when the object to be measure (subject) is the head, it is known as reported in, for example, "Intracerebral penetration of infrared light" by Patric W. McCormic et al, Journal of Neurosurgery published in February, 1992, Vol. 76, paragraphs 315-318) that for the distance between the irradiation position and the detection position being at least 30 mm, detection light transmits through the skin and skull to reach the surface portion of the cerebrum, i.e., the cerebral cortex. It is also known from characteristics of light propagation in the living body that information from a location which lies on a perpendicular vertical to the surface of the living body and extending to the interior of the living body from an intermediate point between the irradiation and detection positions is contained most richly in light detected at that detection position. Such characteristics are reported in, for example, "Monte Carlo simulation of photon path distribution in multiple scattering media" by Shecha Feng et al, SPIE, Proceedings of photon migration and imaging in random media and tissues, Vol. 1888, paragraphs 78-89, (1993).

The living body optical measurement system of the present invention needs a number of light irradiation means and a number of light receiving means for measurement at many positions but as will be described in embodiments to be described later, the system is effective to measurement at a partial position and images can be obtained through a simplified arithmetic processing in which measurement results obtained at a plurality of measuring points are interpolated in association with the respective measuring points.

DESCRIPTION OF THE PREFERRED EMBODIMENTS

Embodiment 1

Embodiments of the present invention will be described hereinafter.

Figure 1:
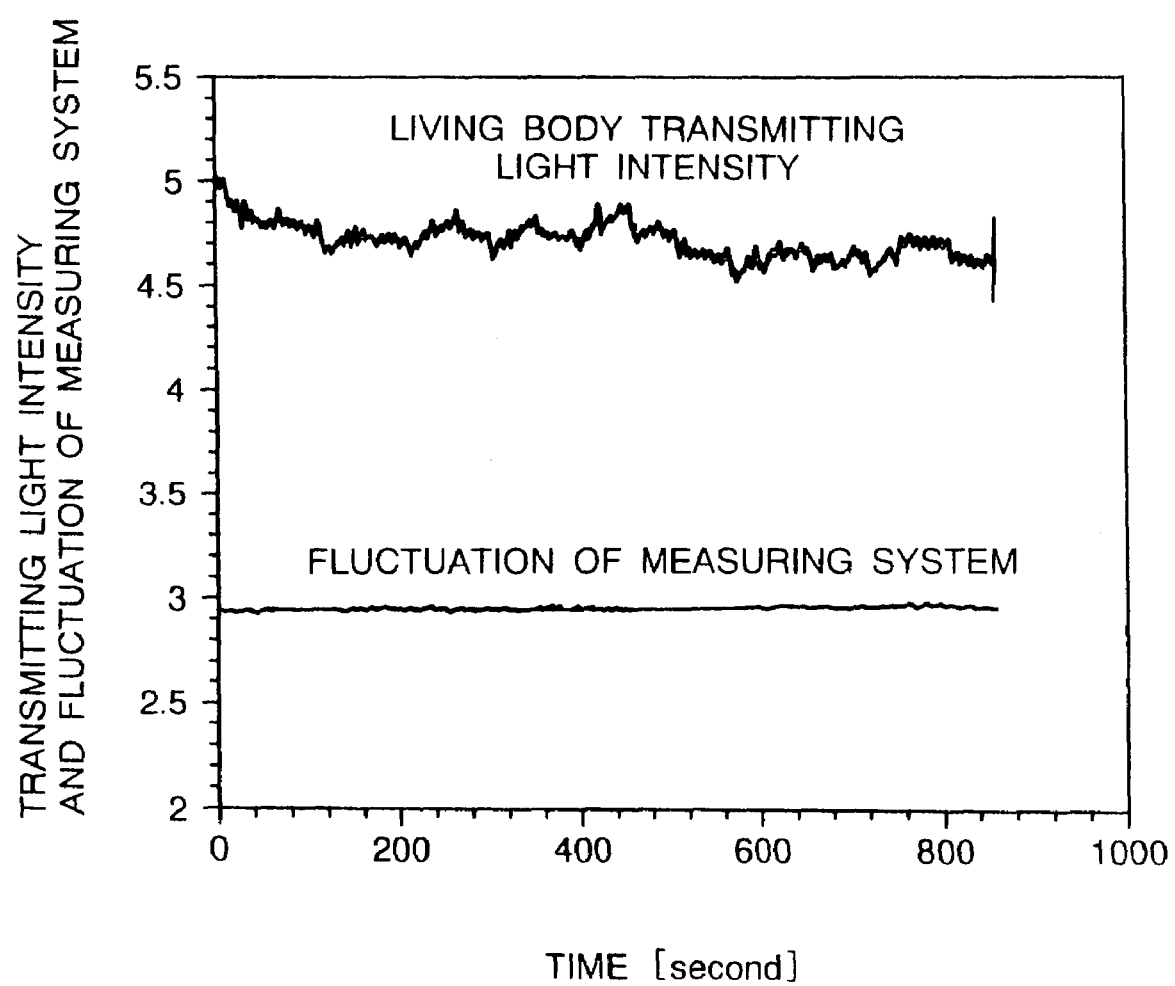
FIG. 1 is a graph showing fluctuation in living body transmitting light intensity obtained with a conventional system.
Figure 2:
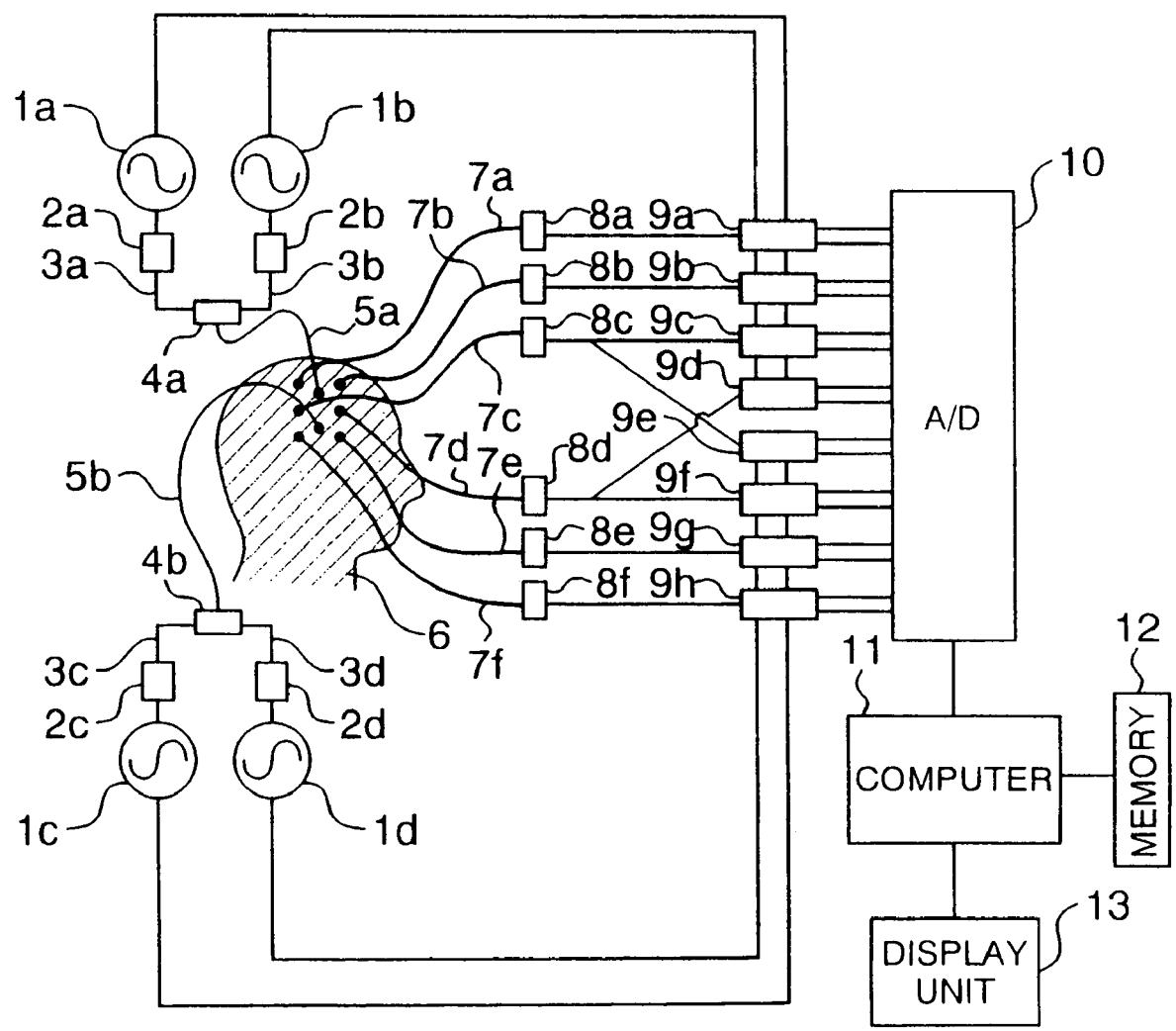
FIG. 2 is a block diagram showing the construction of an embodiment of a living body optical measurement system according to the present invention.

FIG. 2 shows the construction of an embodiment of a living body optical measurement system according to the present invention. The present embodiment is an example in which the living body optical measurement system is applied to the measurement of a change in hemodynamic movement attributable to a cerebral function (a relative change amount of concentration of hemoglobin oxide and reduced hemoglobin). A specified portion of the cerebrum is related to control of an in vivo specified function (for example, moving a part of a body such as fingers) and the hemodynamic movement at the specified cerebral portion is changed by activating the specified function. In one form of the present embodiment, the living body optical measurement system can also be used to measure changes in hemodynamic movement under the application of a load for activation of the aforementioned specified function, for example, moving fingers and display measured changes in the form of a contour map on a two-dimensional plane image indicative of the cerebral portion.

As shown in FIG. 2, there are provided in the present embodiment a plurality of light sources $2a$ to $2d$ having different wavelengths (the light sources $2a$, $2c$ and the light sources $2b$, $2d$ having the same wavelengths, respectively, which are in the range of from visible rays to near infrared rays), modulators for modulating the intensity of light rays of the plurality of light sources $2a$ and $2b$ ($2c$ and $2c$) by means of oscillators $1a$ and $1b$ ($1c$ and $1d$) having mutually different frequencies, a plurality of light irradiation means for irradiating light rays from couplers $4a$ ($4b$), adapted to couple an intensity-modulated light ray propagating through an optical fiber $3a$ ($3c$) and that propagating through an optical fiber $3b$ ($3d$), onto different positions on the scalp of a subject 6 standing for an object to be examined through the medium of optical fibers $5a$ ($5b$), and a plurality of light receiving means comprised of photodetectors $8a$ to $8f$ provided for a plurality of optical fibers $7a$ to $7d$ for light detection and a plurality of light detection optical fibers $7e$ and $7f$ having their tip ends positioned near the light irradiation positions of the plurality of light irradiation means at locations equidistant (assumed herein to be 30 mm) from the light irradiation positions. Living body transmitting light rays are collected to optical fibers by means of the six light detection optical fibers $7a$ to $7f$ and are photoelectrically converted by the photodetectors $8a$ to $8f$, respectively. The light receiving means is operable to detect and convert light reflected inside the subject into an electric signal and a photoelectric conversion element represented by a photomultiplier tube or a photodiode is used as the photodetector 8.

Electric signals indicative of the living body transmitting light intensity levels which are photoelectrically converted by the photodetectors $8a$ to $8f$ (hereinafter referred to as living body transmitting light intensity signals) are inputted to lock-in amplifiers $9a$ to $9h$, respectively. Since the photodetectors $8c$ and $8d$ detects living body transmitting light intensity levels collected by the light detection optical fibers $7c$ and $7d$ which are equidistant from both of the optical fibers $5a$ and $5b$, signals from the photodetectors $8c$ and $8d$ are split into two systems so as to be inputted to the lock-in amplifiers $9c$ and $9e$ and the lock-in amplifiers $9d$ and $9f$. The intensity modulation frequencies from the oscillators $1a$ and $1b$ are inputted, as reference frequencies, to the lock-in amplifiers $9a$ to $9d$ and the intensity modulation frequencies from the oscillators $1c$ and $1d$ are inputted, as reference frequencies, to the lock-in amplifiers $9e$ to $9h$. Accordingly, living body transmitting light intensity signals associated with the light sources $2a$ and $2b$ are separately delivered out of the lock-in amplifiers $9a$ to $9d$ and living body transmitting light intensity signals associated with the light sources $2c$ and $2d$ are separately delivered out of the lock-in amplifiers $9e$ to $9h$.

Exemplarily, for contour map display, the separated transmitting light intensity signals of individual wavelengths delivered out of the lock-in amplifiers $9e$ to $9h$ are subjected to analog to digital conversion by an analog to digital converter 10 and are then stored in a memory 12 provided internally or externally of a computer 11. During or after measurement, the computer 11 uses the transmitting light intensity signals stored in the memory to calculate relative change amounts of concentration values of hemoglobin oxide and reduced hemoglobin which are to be determined from detection signals at individual detection points and stores the calculated amounts in the memory 12 as time-variable information at a plurality of measuring points m. The above calculation will be described later in greater detail. A display controller 30 converts the signals stored in the memory means 12 into display signals for a display unit 13 such as a CRT and displays them on the display unit 13. In the display signals, measuring positions are converted into coordinates on the display plane of the subject and treated as signals for intensity signal (relative change amounts of concentration values of hemoglobin oxide and reduced hemoglobin) contour map display at the coordinate positions.

By using the living body optical measurement system according to the present embodiment, relative change amounts of concentration values of hemoglobin oxide and reduced hemoglobin in the living body can be measured easily at a high speed. The expanded construction in which the number of light incident points (light irradiation positions) and the number of light detection points are increased can be feasible with ease by increasing the number of intensity modulation frequencies of the light sources, of the light sources, of the photodetectors and of the lock-in amplifiers. With the present living body optical measurement system used, the spectroscopic positions and the light irradiation positions can be separated in accordance with the intensity modulation frequencies and therefore, even when the number of the light irradiation positions is increased, it suffices that the number of wavelengths of irradiation light rays at the respective light irradiation positions equals the number of absorbers to be measured, and the wavelength of an irradiation light ray need not particularly be changed for the respective light irradiation positions. Accordingly, the number of wavelengths of irradiation light rays used is small and an error due to the influence of scattering which changes with the wavelength can be decreased.

Figure 3:
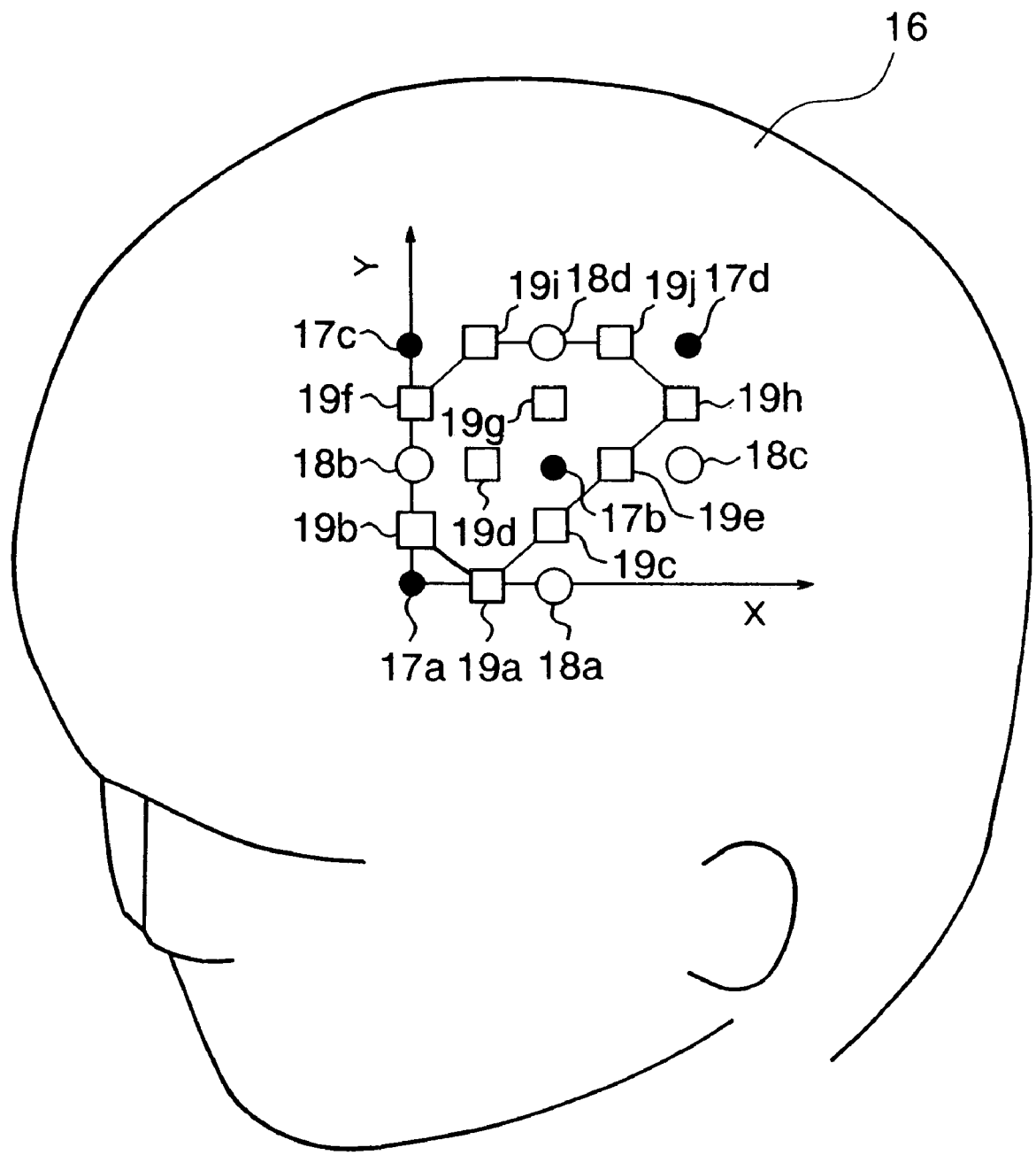
FIG. 3 is a diagram for explaining an embodiment of an imaging method using the measuring system of FIG. 2.

FIG. 3 is a diagram for explaining an embodiment of an imaging method according to the present invention which uses the living body optical measurement system, showing the relation among the light incident point, the light detection point and the measuring point in the above method. The imaging method of the present embodiment is a method for preparing images of relative change amounts of concentration values of hemoglobin oxide and reduced hemoglobin at the head of a subject, wherein four incident points and four detection points are provided at the left temporal participating in the motion function of right fingers of the subject so as to measure living body transmitting light intensity levels and results of measurement obtained under the application of a load of right-finger motion and a load of left-finger motion are imaged.

As shown in FIG. 3, light incident points 17a to 17d and detection points 18a to 18d are disposed on the left temporal of a subject 16. Here, the respective light incident points are in correspondence relationship with the respective detection points through tens sets of 17a-18a, 17a-18b, 17b-18a, 17b-18b, 17b-18c, 17b-18d, 17c-18b, 17c-18c, 17d-18c and 17d-18d. The distance between the corresponding light incident point and detection point is 30 mm. Further, as described in the previously-described "Monte Carlo simulations of photon path distribution in multiple scattering media" by Shechao Feng et al, time-variable changes in the relative change amounts of concentration values of hemoglobin oxide and reduced hemoglobin to be determined from measured signals at the respective detection points best reflect information from an intermediate point between the corresponding incident point and detection point and hence, presumptive measuring points 19a to 19j are each set in the middle of the correspondence relation between each incident point and each detection point. Information at the presumptive measuring points 19a to 19j is determined and the magnitude of the information is displayed in the form of a contour map, a light and shade map or a color discrimination map on the two-dimensional plane as shown in FIG. 3.

Next, there will be described an embodiment of a method according to the present invention for determining relative change amounts of concentration values of hemoglobin, that is, changes in concentration values of hemoglobin at a specified cerebral portion obtained when a specified in vivo function (for example, moving a part of body such as fingers) is activated, from measured signals at the respective light detection points.

Figure 4:
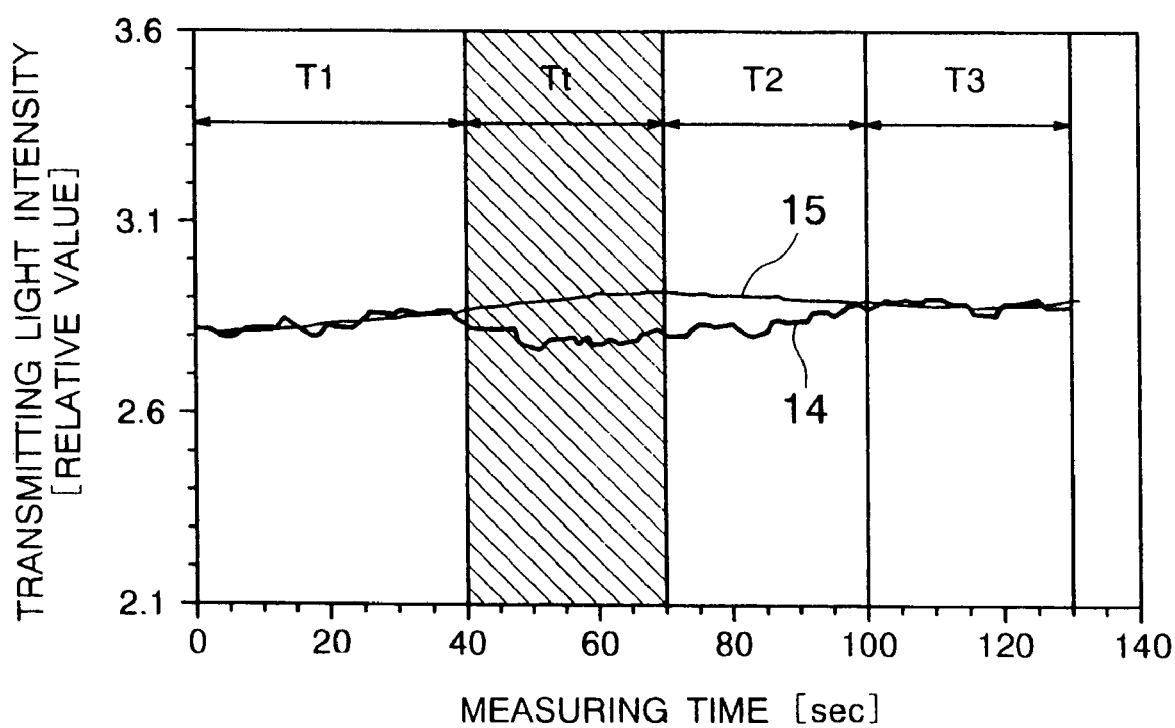
FIG. 4 is a graph depicting a time-variable change in measured signal at a measuring point in the above embodiment and a time-variable change in estimated non-load signal 15 determined from the measured signal.

FIG. 4 is a graph illustrating a measured signal 14 at one of the detection points 18a to 18d of the living body optical measurement system and a time-variable change in estimated non-load signal 15 determined from the measured signal 14 in the embodiment of FIG. 3. In the graph, abscissa represents measuring time and ordinate represents relative concentration change amount.

The estimated non-load signal 15 is determined by removing from the measured signal 14 signals occurring during time Tt for a load to be applied (loading time) and during time T2 for the signal to recover its intact form following loading (relaxation time) and fitting an arbitrary function to the measured signal 14 occurring during load preceding time T1 and load succeeding time T3 through the use of the method of least squares. The present embodiment is handled by using a quadratic linear polynomial as the arbitrary function and setting respective times to T1=40 seconds, T2=30 seconds, Tt=30 seconds and T3=30 seconds.

Figure 5:
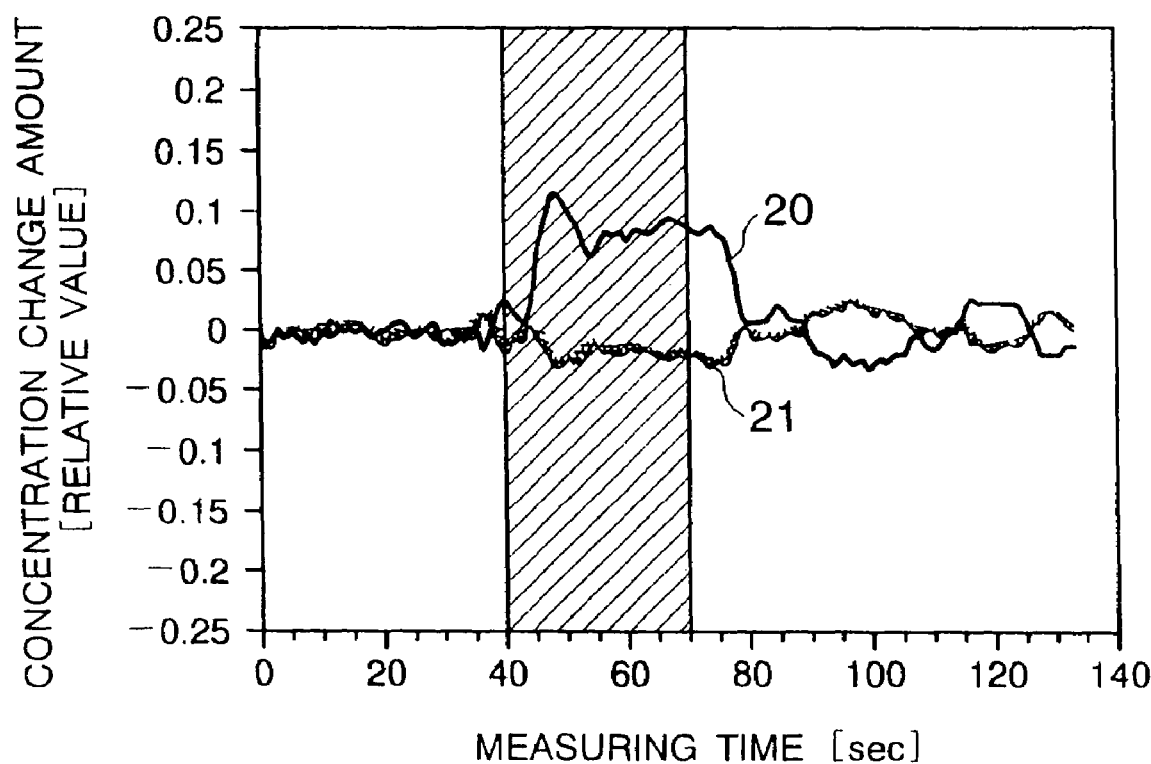
FIG. 5 is a graph depicting a time-variable change in relative change amount of hemoglobin concentration at a measuring point in the above embodiment.

FIG. 5 is a graph illustrating time-variable changes in relative change amounts of concentration values of hemoglobin oxide and reduced hemoglobin (hereinafter represented by $\Delta$Coxy(t) signal 20 and $\Delta$Cdeoxy(t) signal 21, respectively) at one measuring point. In the graph, abscissa represents measuring time and ordinate represents relative concentration change amounts. A hatched time interval corresponds to load applying time (motion period of right fingers). From the measured signal 14 and estimated non-load signal 15 of two wavelengths indicated in FIG. 4, the above relative change amounts of concentration value of hemoglobin oxide and reduced hemoglobin (HbO2, Hb) under the application of a load are determined through the following arithmetic operation processing.

For a wavelength $\lambda$, the relation between estimated non-load signal Str($\lambda$, t) and light source intensity I0($\lambda$) is given by the following equation (2) by separating in vivo light attenuation into scattering and absorption:

$$-\text{Ln}\{\text{Str}(\lambda, t)/\text{I0}(\lambda)\} = \epsilon\text{oxy}(\lambda) \cdot \text{Coxy}(t) \cdot d + \epsilon\text{deoxy}(\lambda) \cdot \text{Cdeoxy}(t) \cdot d + A(\lambda) + S(\lambda) \quad (2)$$

where
- $\epsilon$oxy($\lambda$): extinction coefficient of hemoglobin oxide at wavelength $\lambda$
- $\epsilon$deoxy($\lambda$): extinction coefficient of reduced hemoglobin at wavelength $\lambda$
- A($\lambda$): attenuation due to absorption by other substances than hemoglobin at wavelength $\lambda$
- S($\lambda$): attenuation due to scattering at wavelength $\lambda$
- Coxy(t): concentration of hemoglobin oxide at measuring time t
- Cdeoxy: concentration of reduced hemoglobin at measuring time t d: in vivo effective optical path length (in a region of interest)

Also, the relation between measured signal $Sm(\lambda, t)$ and light source intensity $I0(\lambda)$ is given by the following equation (3):

$$-\ln\{Sm(\lambda,t)/I0(\lambda)\} = \epsilon oxy(\lambda).\{Coxy(t)+C'oxy(t)+Noxy(t)\}.d + \epsilon deoxy(\lambda).\{Cdeoxy(t)+C'deoxy(t)+Ndeoxy(t)\}d + A'(\lambda) + S'(\lambda) \quad (3)$$

where

C'oxy(t): change in concentration of hemoglobin oxide under the application of load at measuring time t C'deoxy(t): change in concentration of reduced hemoglobin under the application of load at measuring time t Noxy(t): noise or high frequency fluctuation in concentration of hemoglobin oxide at measuring time t Ndeoxy(t): noise or high frequency fluctuation in concentration of reduced hemoglobin at measuring time t Here, if $A(\lambda)$ and $S(\lambda)$ remain unchanged under loading and unloading, that is, if a change in the measured signal under the application of load is due to only changes in concentration values of hemoglobin oxide and reduced hemoglobin, the difference between equations (2) and (3) is given by the following equation (4):

$$\ln\{Str(\lambda,t)/Sm(\lambda,t)\} = \epsilon oxy(\lambda)\{C'oxy(t)+Noxy(t)\}d + \epsilon deoxy(\lambda)\{C'deoxy(t)+Ndeoxy(t)\}d \quad (4)$$

Here, time-variable changes in relative change amounts of concentration values of hemoglobin oxide and reduced hemoglobin under the application of load are represented by $\Delta Coxy(t)$ and $\Delta Cdeoxy(t)$ and defined by the following equation:

$$\Delta Coxy(t)=\{C'oxy(t)+Nox(t)\}d \Delta Cdeoxy(t)=\{C'deoxy(t)+Ndeoxy(t)\}d \quad (5)$$

Usually, it is difficult to specify d and therefore, the dimension of the concentration change amount is herein the product of concentration and distance d.

But, in equation (5), distance d acts equally on $\Delta Coxy$ and $\Delta Cdoxy$ and so equation (5) is considered as indicating relative change amounts of hemoglobin concentration values. When two wavelengths are used for measurement, obtained equation (4) is reduced to a simultaneous equation with two unknowns for $\Delta Coxy(t)$ and $\Delta Cdeoxy(t)$, so that $\Delta Coxy(t)$ and $\Delta Cdeoxy(t)$ can be determined from estimated non-load signal $Str(\lambda, t)$ and measured signal $Sm(\lambda, t)$ for each wavelength. Further, what is indicated by $\Delta Coxy(t)$ and $\Delta Cdeoxy(t)$ during a period other than loading time and relaxation time can be formulated by C'oxy(t)=0 and C'deoxy(t)=0, which indicate noises or high frequency fluctuations, attributable to the living body, of concentration of hemoglobin oxide and reduced hemoglobin. The above procedure is carried out for 0 to 140 seconds to obtain $\Delta Coxy(t)$ signal 20 and $\Delta Cdeoxy(t)$ signal 21 of FIG. 5.

Figure 6:
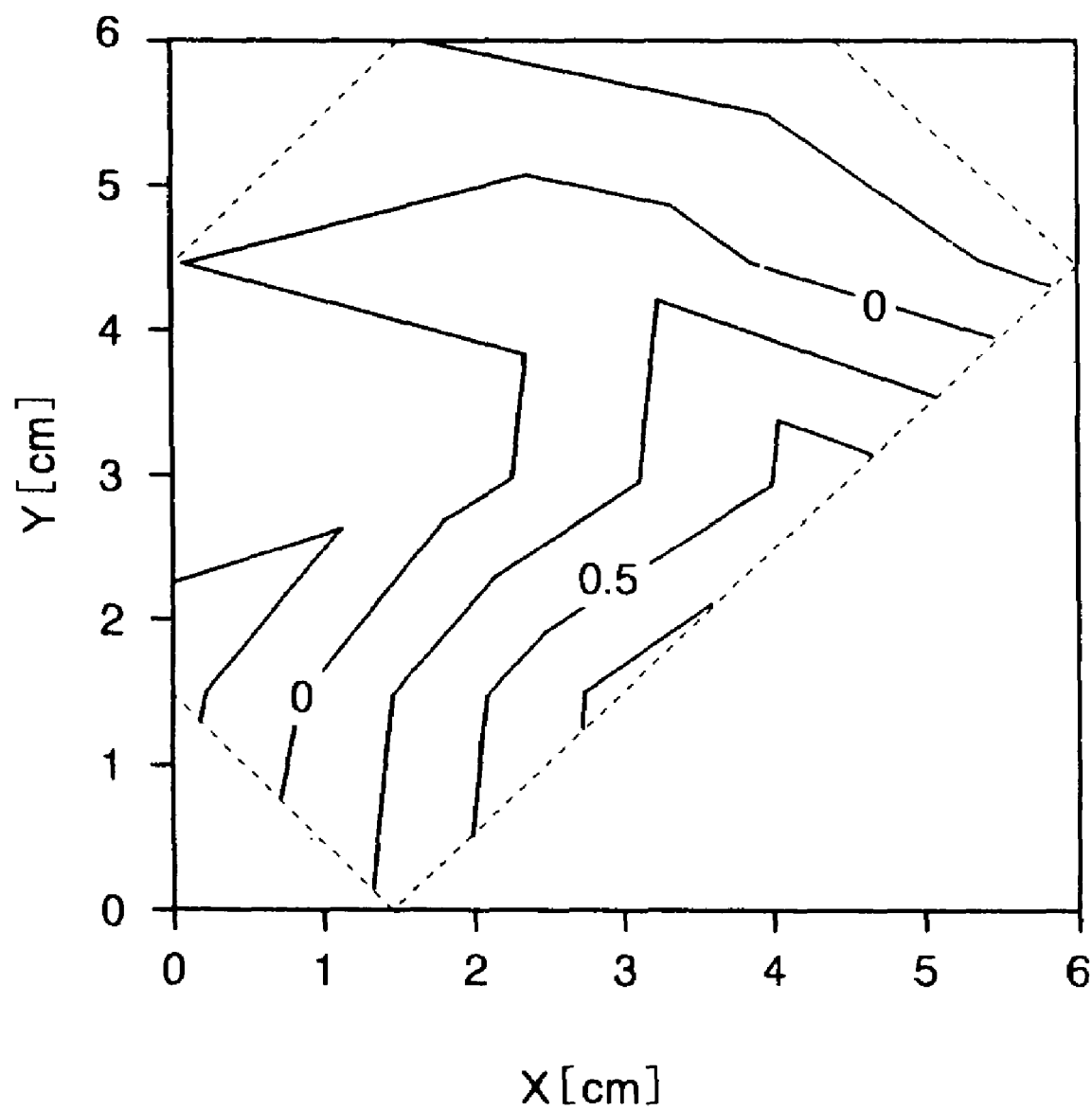
FIG. 6 is a graph depicting a topography image in the above embodiment.
Figure 7:
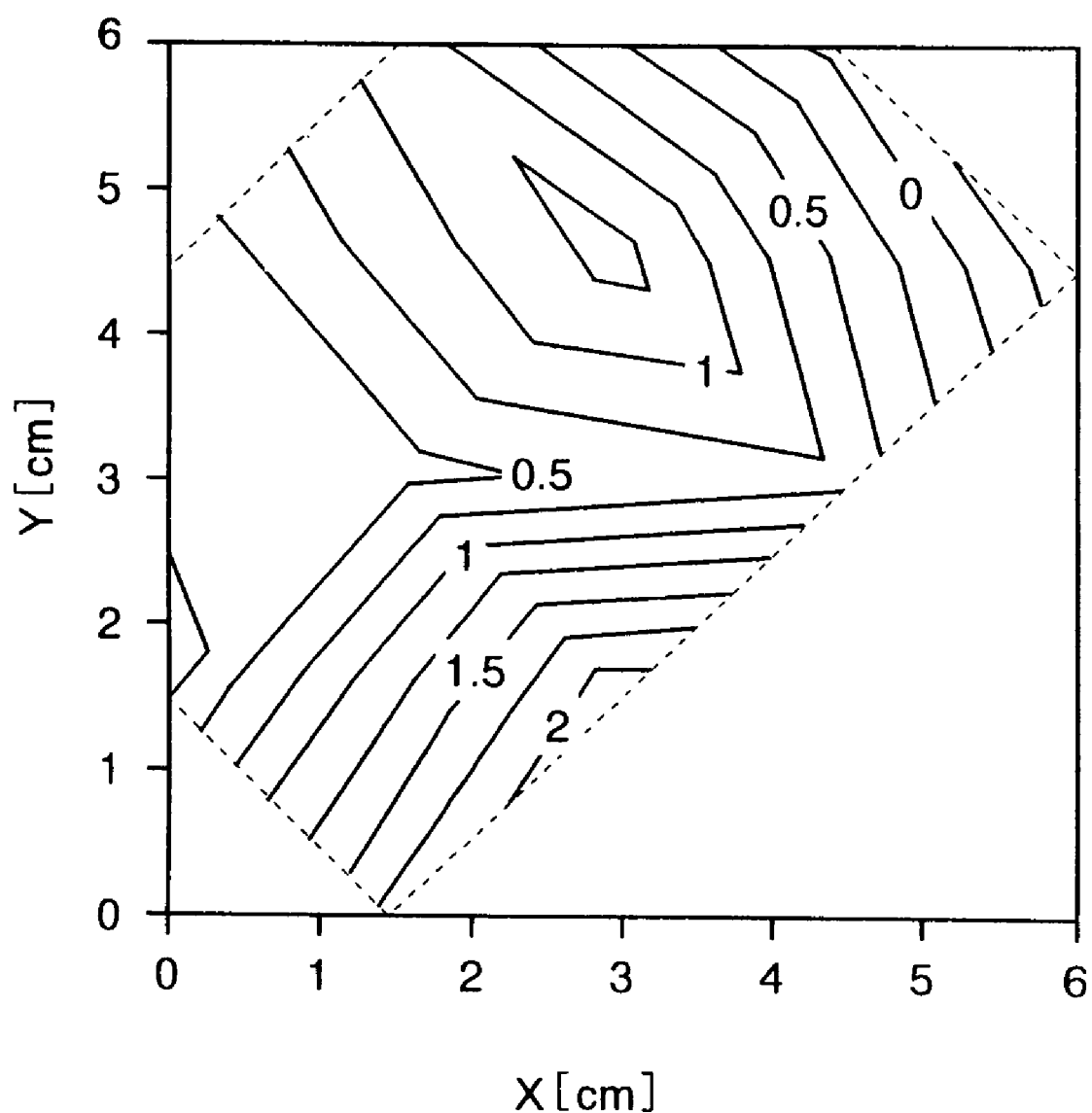
FIG. 7 is a graph depicting another example of the topography image in the above embodiment.

FIGS. 6 and 7 show contour map images (topographic images) prepared from time-variable changes in relative change amounts of concentration values of hemoglobin oxide at the respective measuring points under the application of loads of left-finger motion and right-finger motion of a subject, respectively. A method for preparation of the topography images is such that a time integral (alternatively, time average) of relative change amount $\Delta Coxy(t)$ signal 20 during load applying time (hatched period in FIG. 5) is calculated by the computer 11 and values between individual measuring points are determined through linear interpolation in X-axis and Y-axis directions. In addition to the contour map, the topographic image may include a monochromatic light and shade image and a discrimination display in color. It will be seen by comparing the images of FIGS. 6 and 7 that the concentration of hemoglobin oxide clearly increases at specified positions during the right hand motion. By displaying this type of spatial distribution information as images, rapid and easy recognition of measurement results can be ensured. While the images shown in FIGS. 6 and 7 are prepared from the time integral values of concentration relative change amounts during the load applying time, a topography image can also be prepared similarly from relative change amounts of concentration values of hemoglobin oxide which are measured every constant measuring time at the respective measuring points. When a plurality of topographic images thus prepared in accordance with order of the measuring time points or displayed as a moving picture, time-variable changes in the relative change amounts of concentration values of hemoglobin oxide can be obtained.

Further, by calculating time-variable changes in relative change amounts of concentration values of hemoglobin oxide at an arbitrary measuring point as well as a self correlation function and a mutual correlation function of time-variable changes in relative change amounts of concentration values of hemoglobin oxide at that arbitrary measuring point and another measuring point, a topographic image can be prepared from the correlation functions at the individual measuring points. The correlation function at each measuring point is a function defined by time shift $\tau$ and therefore, by preparing topography from a value of the correlation function at the same time shift $\tau$ and displaying the topography in accordance with order of $\tau$ or displaying it in the form of a moving picture, hemodynamic movement which changes by participating in activation of the cerebral function can be visualized.

Here, the relative change amount of concentration of hemoglobin oxide is typically used for explanation but the relative change amount of concentration of reduced hemoglobin or the total hemoglobin concentration change amount which is calculated by adding the relative change amount of concentration of hemoglobin oxide and the relative change amount of concentration of reduced hemoglobin may be used to prepare topographic in a similar way.

Figure 8:
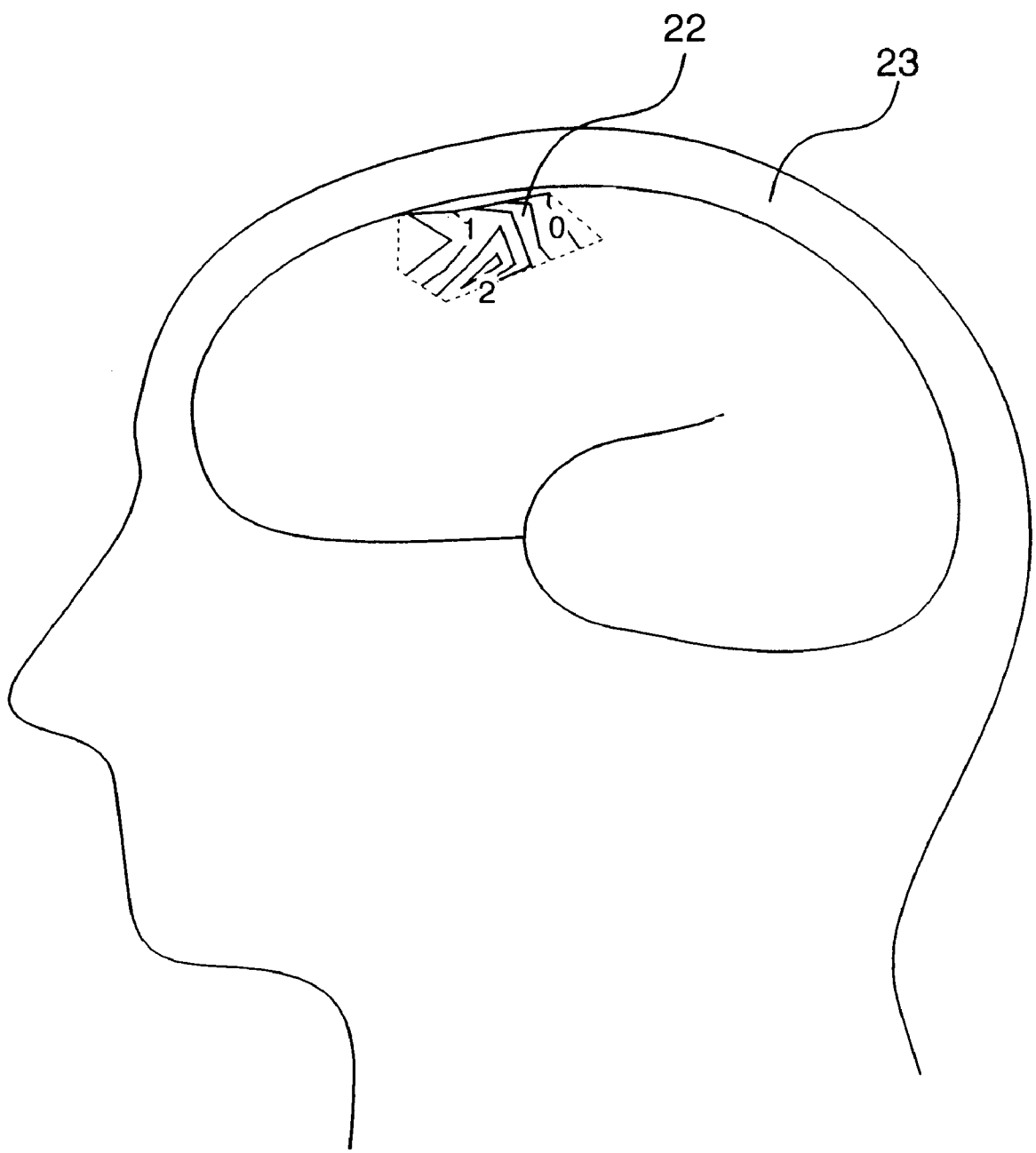
FIG. 8 is a graph depicting an example of display of topography image in the above embodiment.

FIG. 8 shows a display example in which a topography image 22 prepared through the above-described method is superimposed on a cerebral surface image 23. Since the topographic image 22 is illustrative of a change in cerebral hemodynamic movement which changes in association with an biological function, it is preferably displayed while being superimposed on the cerebral surface image. The cerebral surface image 23 is measured through three-dimensional MRI or three-dimensional X-ray CT and is displayed. The topographic image 22 is subjected to coordinate conversion such that coordinates of individual measuring points are positioned on the cerebral surface and values between individual measuring points subject to the coordinate conversion are interpolated to prepare the topographic image. When the prepared topographic image 22 is displayed while being superimposed on the cerebral surface image 23, color of the overlying topographic image 22 is made to be semitransparent to allow the underlying cerebral surface image to be seen transparently.

Figure 9:
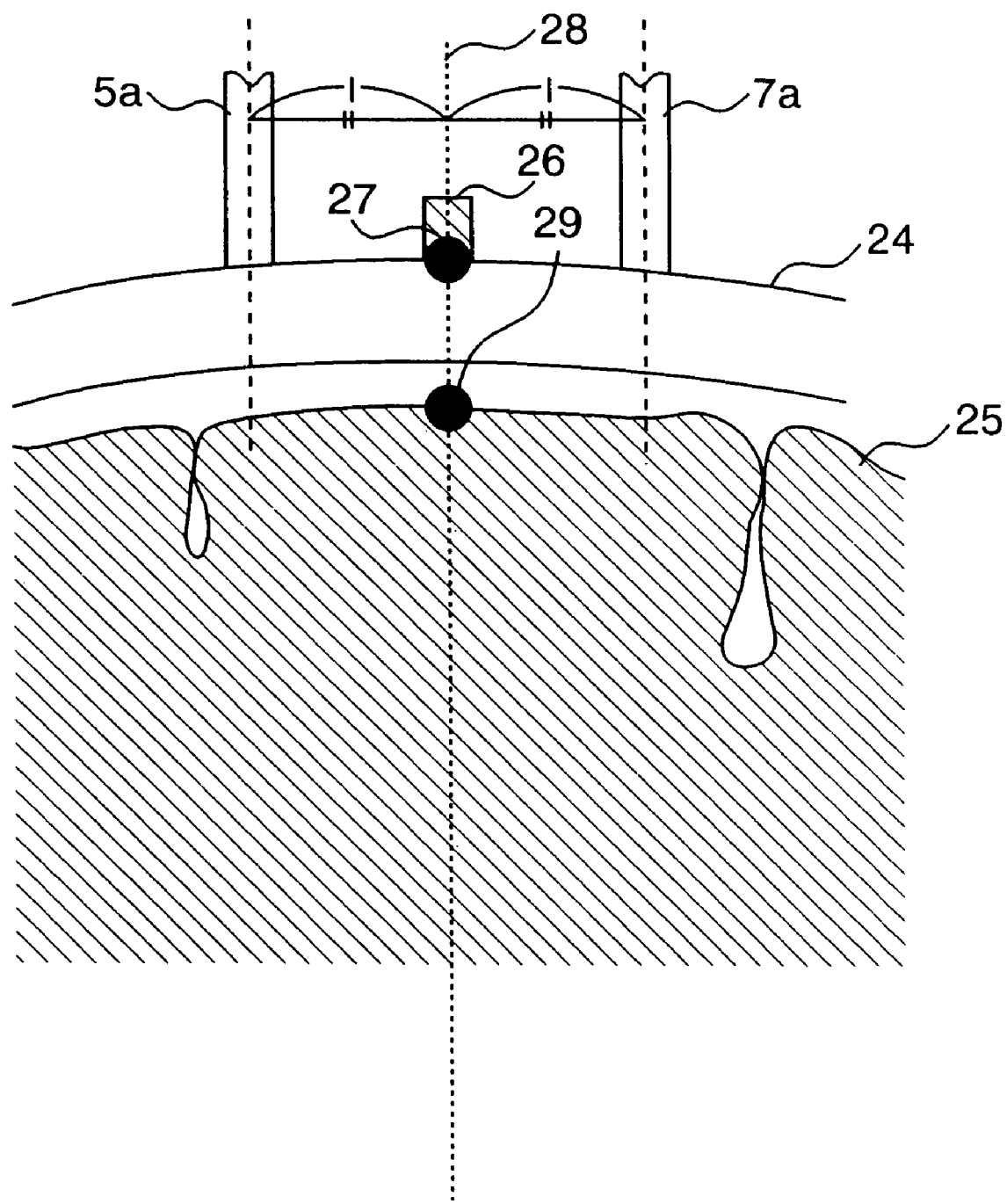
FIG. 9 is a diagram for explaining a method for coordinate conversion in another embodiment of the living body optical measurement system of the present invention.

FIG. 9 shows a diagram for explaining a measuring point coordinate converting method. A method of taking images of the form of three-dimensional MRI or three-dimensional X-ray CT will hereunder be described specifically. In FIG. 9, 5a designates an optical fiber for irradiation and 7a an optical fiber for detection. Information at a portion on the center line between these fibers is presumed for use as information at a desired measuring point. This is because a portion is used at which the supply of the quantity of light from the irradiation fiber is maximized and the signal from an object to be measured is maximized. By performing imaging while disposing a marker at the measuring point 29 which is presumptively set by the living body optical measurement system, a skin and skeleton image 24, a cerebral image 25 and a marker image 26 can be displayed on the basis of the imaged form information. The images picked up as above have three-dimensional coordinate information. Thus, a perpendicular 28 passing through a measuring point 27 indicated by the marker image 26 and being vertical to the skin surface at the measuring point 27 or the bottom of the marker image 26 is calculated and a point at which the perpendicular intersects the cerebral image 25 is defined as the measuring point 29 subject to the coordinate conversion. As shown in the present embodiment, it is known that when the cerebral function is measured, a change in hemodynamic movement having correlation to load occurs mainly at the cerebral surface (cerebral cortex). For the reasons set forth as above, by using anatomical information, the depth for coordinate conversion of measuring points can be known. But when an object to be measured is another living body organ such as muscles, the depth for coordinate conversion of measuring points cannot sometimes be known from the anatomical information. In applying the present method to the measurement as above, light propagation of living tissue is calculated in advance through numerical calculation based on the Monte Carlo method to determine a depth best contributing to measured signals and coordinates of the measuring point are converted to the thus determined depth.

The topographic image has been described as presumptive display image but a different image display method is available.

For example, a square pixel of arbitrary size having the center of gravity at a presumptive measuring point is set at each presumptive measuring point, each pixel is displayed either in the form of an image in light and shade painted in color in correspondence to a value of each presumptive measuring point, the correspondence being determined in advance, or in the form of a bar graph image indicated by a bar or a length of line which corresponds to a value of each measuring point.

In all image display methods, color arrangement can be selected freely when color is used but for measurement of hemodynamic movement, display in combination of light and shade of red color and light and shade of blue color is preferable. This is because such an image that arterial hemodynamic is red and venous hemodynamic is blue is fixed. For example, the magnitude of positive measured value is displayed in light and shade of red color and the magnitude of negative measured value is displayed in light and shade of blue color.

Embodiment 2

A second embodiment according to the present invention will be described.

Figure 10:
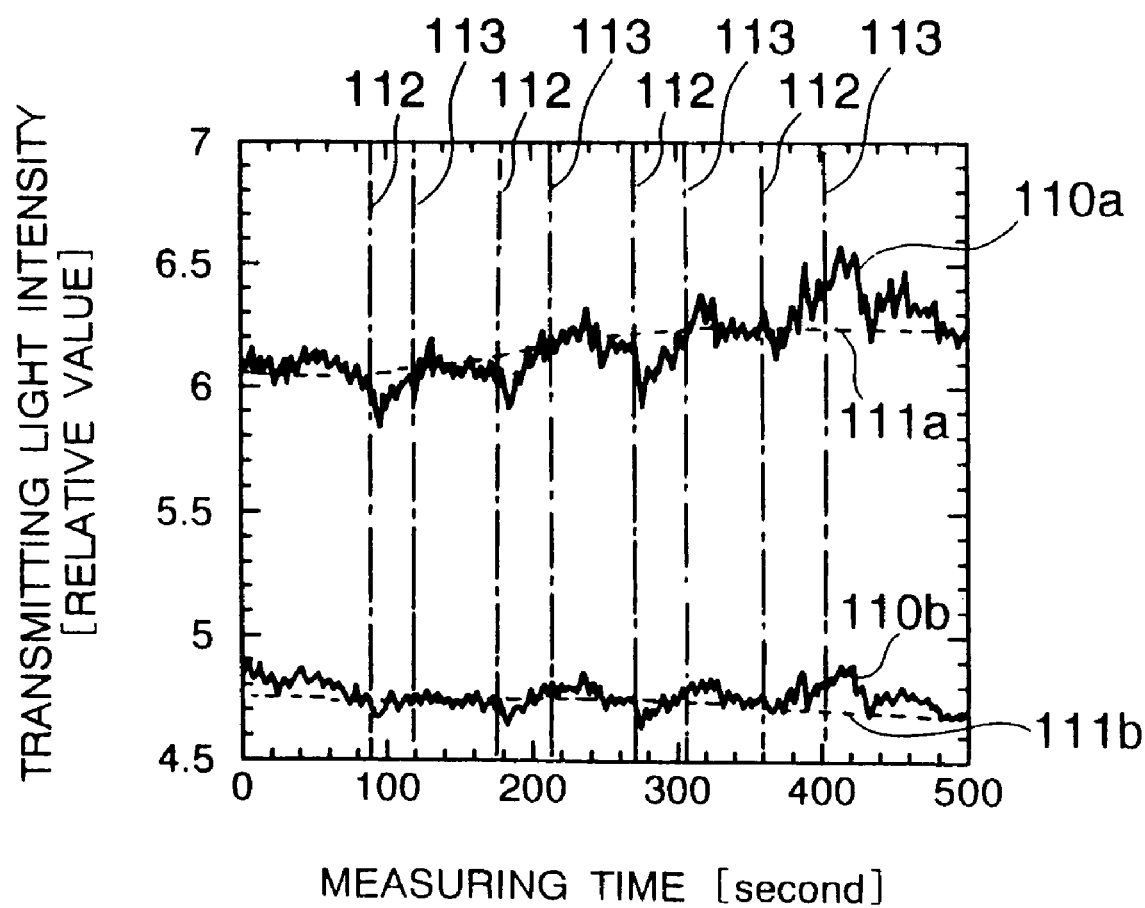
FIG. 10 is a graph showing an example of display in the measuring system of the present invention.

FIG. 10 shows an example of display of measured signals and estimated non-load signals. Displayed measured signals 110a and 110b are output signals from the lock-in amplifier 9a and estimated non-load signals 111a and 111b are calculated from the respective measured signals (calculation method will be described later).

The estimated non-load signals 111a and 111b are displayed on the display unit. In the displayed graph, abscissa represents measuring time and ordinate represents relative values of measured signals indicative of transmitting light intensity levels measured by the living body optical measurement system.

When a load is applied to a subject, a loading start mark 112 indicative of a load application starting time point and a loading end mark 113 indicative of a load application ending time point are displayed in the form of straight lines. In the present embodiment, the cerebral cortex region dominating the right-hand motion is measured from the scalp through the skull and the right-hand or left-hand motion is applied as a load (loads 1 and 3 correspond to the right-hand motion and loads 2 and 4 correspond to the left-hand motion). Although in FIG. 10 all signals occurring throughout the measuring time, only a desired time interval (for example, a time interval including times before and after the loading time) can be displayed easily. Also, if the estimated non-load signals 111a and 111b are each displayed until a desired time point on an extension of the curve indicative of a time-variable change, the measured signals 110a and 110b and the estimated non-load signals 111a and 111b can be displayed simultaneously on real time base during measurement. By simultaneously displaying the measured signals 110a and 110b and the estimated non-load signals 111a and 111b in this manner, a change in hemodynamic movement occurring in the living body can be decided easily by an observer. The estimated non-load signals displayed in advance on real time base can be corrected for display in the phase at which calculation of the estimated non-load signals is settled.

The estimated non-load signals 111a and 111b can be determined by removing signals occurring during the load applying time (loading time) and signals occurring during the time for the signal to recover its intact form following removal of the load (relaxation time) and by fitting an arbitrary function to signals occurring during the remaining period through the method of least squares. Here, the arbitrary function and the relaxation time change with the kind of load and measurement locations and so those meeting the purpose of measurement are inputted through the input unit. In the present embodiment, the arbitrary function in the form of a polynomial of degree five is handled and the relaxation time is set to 30 seconds. Further, for the convenience of watching by the observer, different kinds of color or different kinds of lines can be used for display of signals.

Figure 11A:
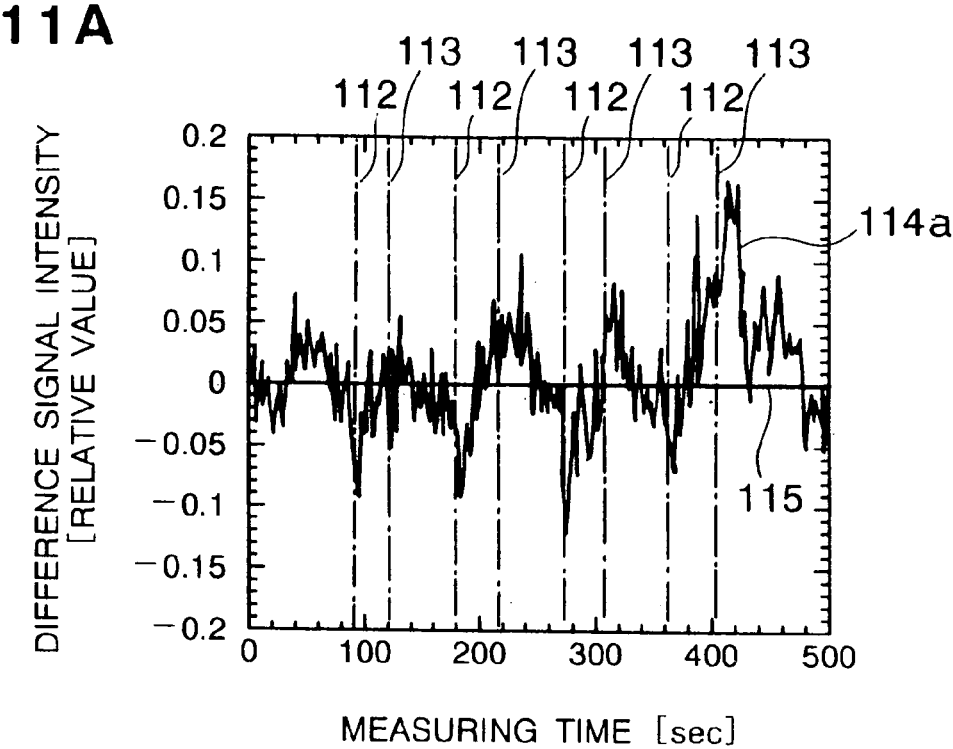
FIGS. 11A and 11B are graphs showing examples of display according to the measuring system of the present invention.
Figure 11B:
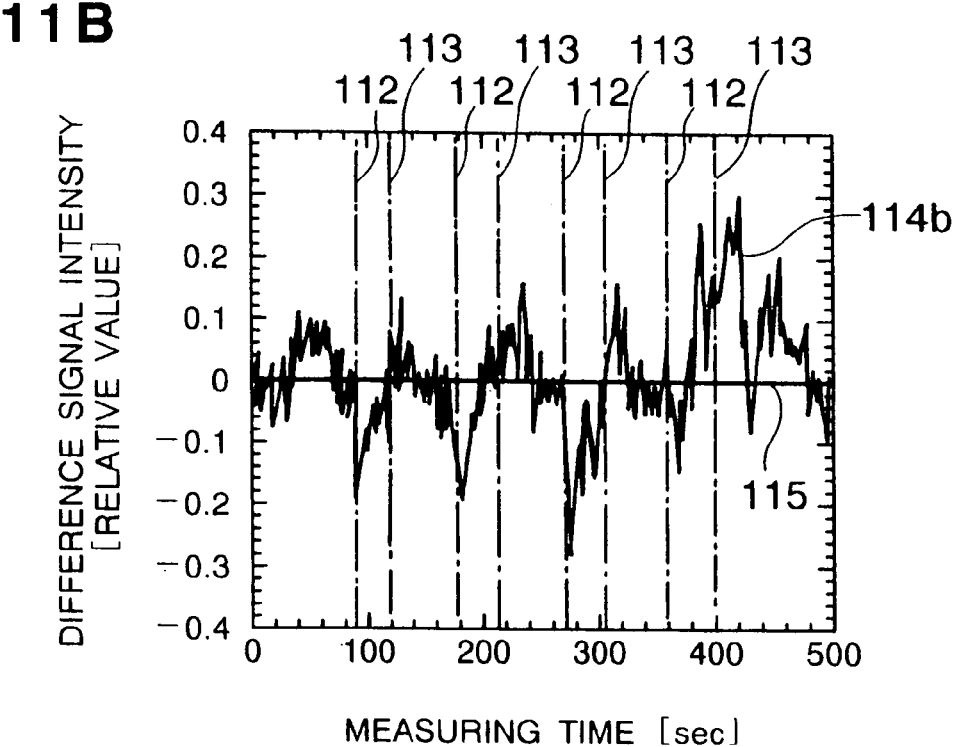

FIGS. 11A and 11B show examples of display of a difference signal between a measured signal and an estimated non-load signal and in these figures, a waveform of a difference signal 114a obtained by calculating the difference between the measured signal 110a and the estimated non-load signal 111a in FIG. 10 and a waveform of a difference signal 114b obtained by calculating the difference between the measured signal 110b and the estimated non-load signal 111b in FIG. 10 are displayed on the display unit. In the displayed graph, abscissa represents measuring time and ordinate represents relative difference signal intensity. Further, when a load is applied to a subject, a load start mark 112 indicative of a load application starting time point and a load end mark 113 indicative of a load application ending time point are displayed in the form of straight lines. Also, the present graph is a graph having its center at 0 and so shows a base line 115.

In the present embodiment, waveforms 114a and 114b are displayed on different coordinate axes for different light source wavelengths but they can be displayed overlapping each other on the same coordinate axis. Also, for the convenience of watching by an observer, different kinds of color or different kinds of lines can be used for display.

Figure 12A:
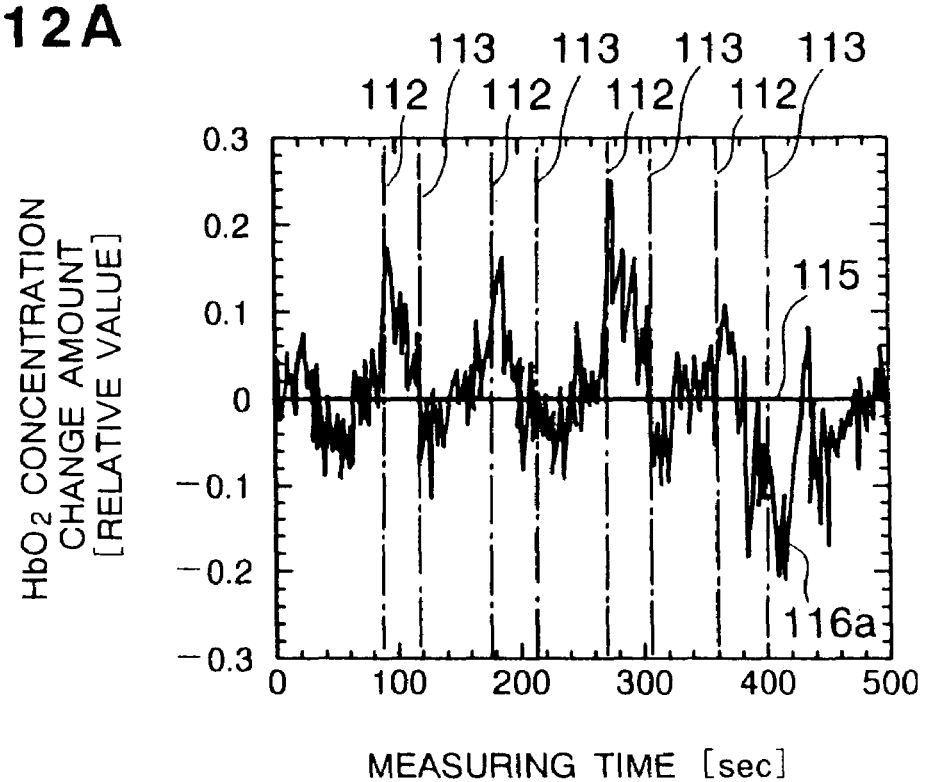
FIGS. 12A and 12B are graphs showing examples of display according to the measuring system of the present invention.
Figure 12B:
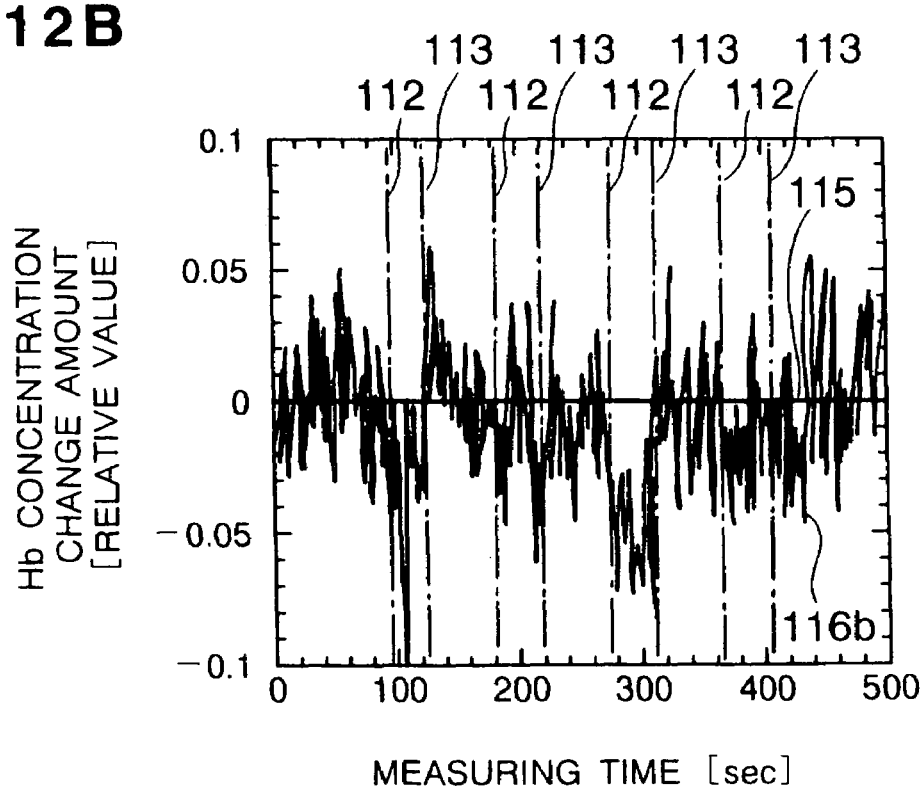

FIGS. 12A and 12B show examples of display of graphs depicting relative change amounts of concentration values of HbO2 and Hb (hereinafter represented by ΔCoxy and ΔCdeoxy, respectively) under the application of load. A waveform of a ΔCoxy signal 116a obtained from the measured signal 110a and estimated non-load signal 111a in FIG. 10 pursuant to equation (5) and a waveform of a ΔCdeoxy signal 116b obtained from the measured signal 110b and estimated non-load signal 111b in FIG. 10 pursuant to equation (5) are displayed on the display unit. In the displayed graph, abscissa represents measuring time and ordinate represents values of ΔCoxy and ΔCdeoxy. Further, a load start mark 112, a load end mark 113 and a base line 115 are also displayed. In the present embodiment, all intervals of measuring time are displayed but only desired time intervals (for example, a period including time points before and after the loading time) can be displayed. Here, the waveforms 116a and 116b are displayed separately on different coordinate axes but they may be displayed overlapping each other on the same coordinate axis. Further, the individual signals may be displayed in different kinds of color or in the form of different kinds of lines and for intuitive understanding by an observer, the ΔCoxy signal 116a may be displayed in, for example, a kind of red color and the ΔCdeoxy signal 116b may be displayed in, for example, a kind of green color. According to the measuring method and display method of the present invention, the correlation between load and measured signal is easy to understand and fluctuation is removed from the measured signal, thus ensuring that accuracy of signals can be increased.

Figure 13:
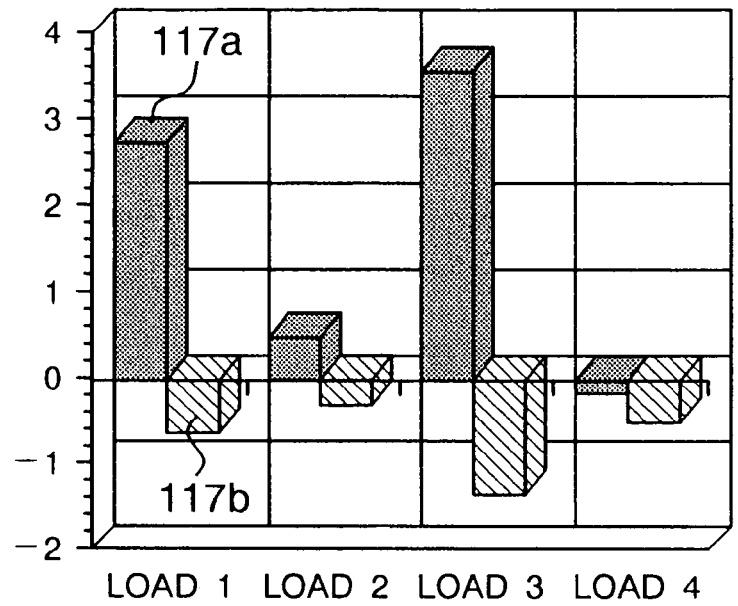
FIG. 13 is a graph showing an example of display according to the measuring system of the present invention.

FIG. 13 shows an example of display of a ΔCoxy loading time integral value 117a and a ΔCdeoxy loading time integral value 117b which are obtained during respective loading times. The ΔCoxy signal 114a and the ΔCdeoxy signal 114b in FIGS. 11A and 11B are time integrated during each loading time to determine the ΔCoxy loading time integral value 117a and ΔCdeoxy loading time integral value 117b, which are displayed in the form of a cubic bar graph for respective load number. Here, abscissa represents load number and ordinate represents ΔCoxy loading time integral value and ΔCdeoxy loading time integral value. Alternatively, a ΔCoxy loading time average value and a ΔCdeoxy loading time average time may be displayed. Also, for the convenience of watching by an observer, display in different colors can be used.

Figure 14:
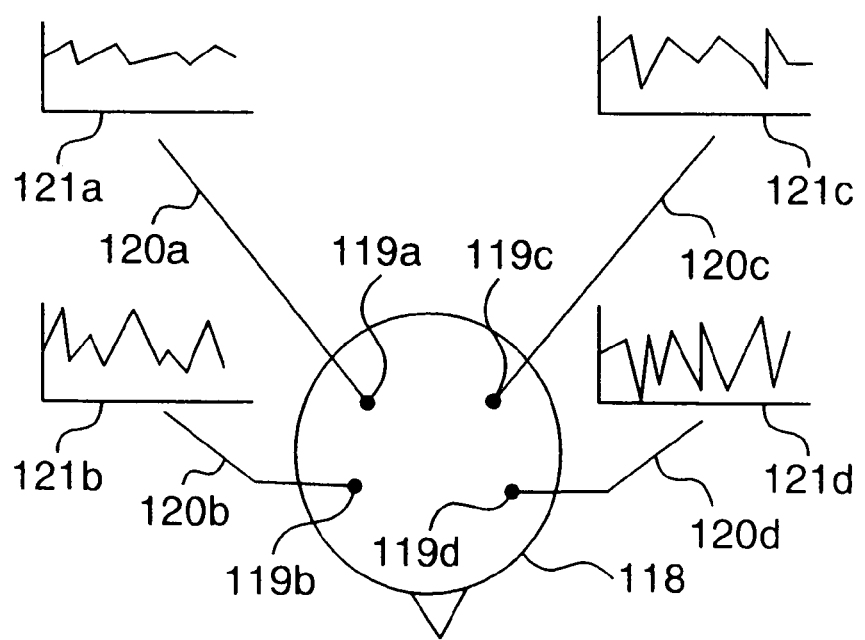
FIG. 14 is a graph showing an example of display according to the measuring system of the present invention.

FIG. 14 shows an example of display when measurement is conducted at a plurality of measuring positions by using the living body optical measurement system. Here, an instance will be described where the portion to be measured is the head and four measuring positions are set on the head.

In the present display example, a measuring portion image 118 of a subject, measuring position marks 119a to 119d representative of set measuring positions, graphs 121a to 121d corresponding to the respective measuring positions and index lines 120a to 120d for indicating the correspondence relation between the respective measuring positions and the respective graphs are displayed on the display unit. Here, a head model figure or a measuring portion tomographic image or measuring portion three-dimensional image of a subject itself imaged by an image diagnostic apparatus represented by an MRI apparatus can be used as the measuring portion image 118.

Embodiment 3

Figure 15:
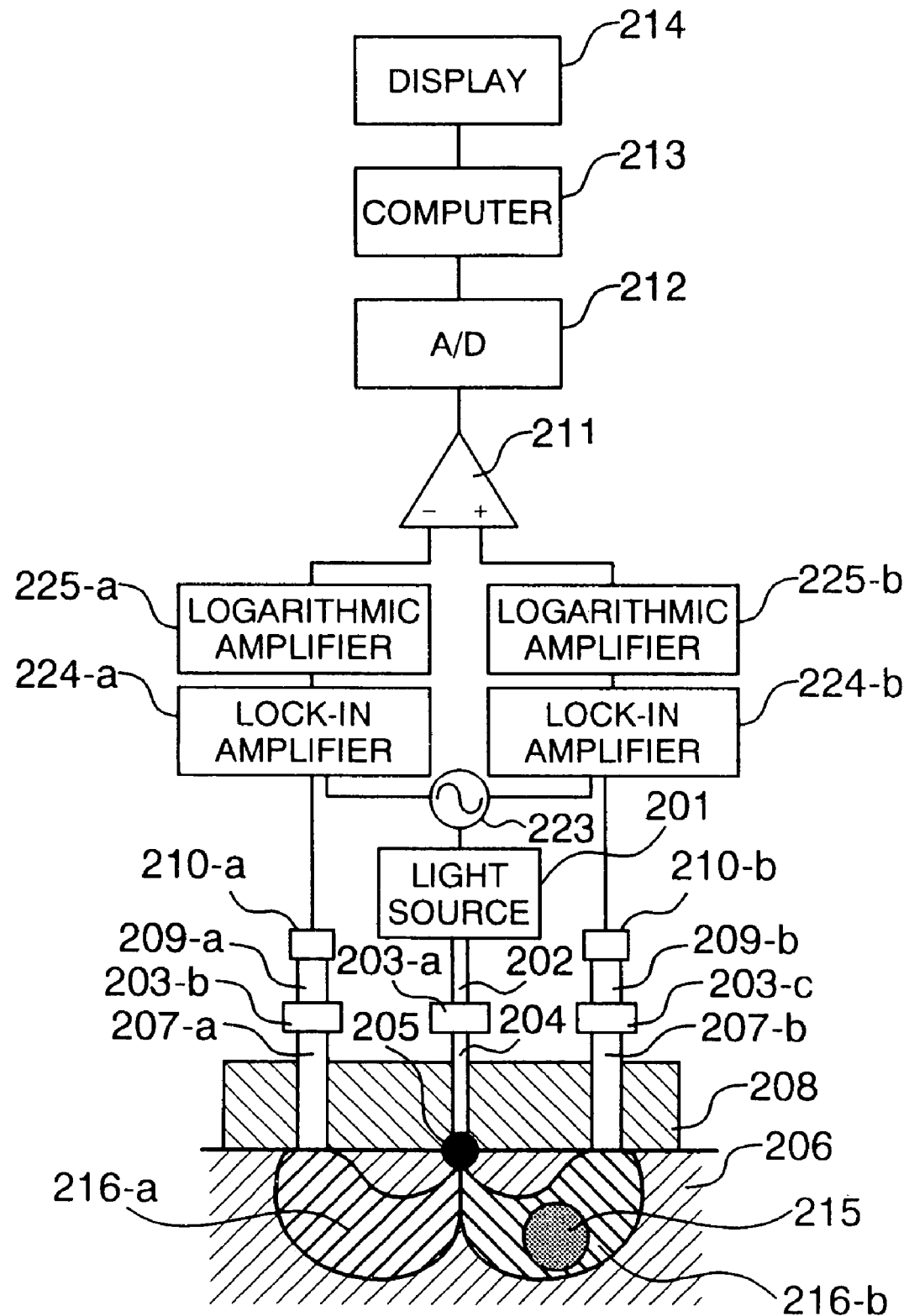
FIG. 15 is a block diagram for explaining the construction of a system according to another embodiment of the present invention.

The schematic construction of embodiment 3 of the living body optical measurement system according to the present invention is shown in FIG. 15.

Light emitted from a light source 201 is collected using a lens system so as to impinge on an optical fiber 202 for light source. The light emitted from the light source is modulated in intensity with a desired frequency f of about 100 Hz to 10 MHz by means of an oscillator 223 in order to remove noises due to external disturbance. Since the light source optical fiber 202 is connected to an optical fiber 204 for light irradiation through an optical fiber coupler 203a, the light from the light source is transmitted to the light irradiation optical fiber 204 and is irradiated on a subject 206 by way of a light irradiation position 205. The wavelength of the light used depends on spectroscopic characteristics of an in vivo substance of interest but when the oxygen saturation amount and the blood amount are measured from concentration values of Hb and HbO2, a single or a plurality of wavelengths can be selected, for use, from light having the wavelength range of from 600 nm to 1400 nm. A semiconductor laser, a titanium/sapphire laser or a light emitting diode can be used as the light source.

Two light detection optical fibers 207a and 207b for detecting light transmitting through the subject 206 and going out of it are disposed at two different sites on the subject 206. In the present embodiment, the two light detection optical fibers 207a and 207b are disposed at two sites which are point symmetrical to a symmetry center of the light irradiation position 205. The light irradiation optical fiber 204 and the light detection optical fibers 207a and 207b are held in place by means of an optical fiber fixing member 208 having its surface painted in black. For simplicity of construction, the light irradiation optical fiber 204, light detection optical fibers 207a and 207b and optical fiber fixing member 208 are integrally formed into a light detection probe to be detailed later. Since the light detection optical fibers 207a and 207b are connected to optical fibers 209a and 209b for photodetectors through optical fiber couplers 203b and 203c, transmitting light rays detected by the light detection optical fibers 207a and 207b are transmitted to photodetectors 210a and 210b and subjected to photoelectric conversion by the photodetectors 210a and 210b, so that transmitting light intensity levels are delivered in the form of electric signal intensity levels. Used as the photodetectors 210a and 210b are photoelectric conversion elements such as for example photodiodes or photo-multiplier tubes.

Of electric signals indicative of transmitting light intensity levels delivered out of the photodetectors 210a and 210b, only frequency components for light intensity modulation of the light source are extracted by lock-in amplifiers 224a and 224b, respectively. While an output from the lock-in amplifier 224a is subjected to logarithmic conversion by a logarithmic amplifier 225a and then inputted to the negative pole of a differential amplifier 211, an output from the lock-in amplifier 224b is subjected to logarithmic conversion by a logarithmic amplifier 225b and subsequently inputted to the positive pole of the differential amplifier 211. As a result, a difference signal between transmitting light intensity levels at the two different sites is delivered out of the differential amplifier 211 as an output signal. The output signal from the differential amplifier 211 is sequentially converted into a digital signal by an A/D converter 212, fetched into a computer 213 and displayed on a display unit 214 as time series data. Here, when a region 215 where the hemodynamic movement changes locally is included in only a view field 216b of the light detection optical fiber as shown in FIG. 15, the measured logarithmic difference signal reflects only a change in hemodynamic movement at the local region 215. On the presupposition that for near infrared rays, hemoglobin serving as a main constituent in hemodynamic dominantly acts on extinction, the meaning of the measured logarithmic difference signal will be described below.

Where measuring time is t, light source wavelength is λ, irradiation light intensity is I0(t), concentration values of hemoglobin oxide and reduced hemoglobin are Cox(t) and Cdeox(t), respectively, changes in concentration values of hemoglobin oxide and reduced hemoglobin which occur at the local region 215 are ΔCox(t) and ΔCdeox(t), respectively, extinction coefficients for light source wavelength λ of hemoglobin oxide and reduced hemoglobin are ϵox(λ) and ϵdeox (λ), respectively, attenuation due to scattering and absorption caused by other constituents than hemoglobin is Ds and weight coefficient caused by scattering is d, transmitting light intensity signal Id(t) detected by the photodetector 210b is given by the following equation (6) and transmitting light intensity signal Id'(t) detected by the photodetector 210a is given by the following equation (7):

$$Id(t) = Ds \cdot \exp[-[\epsilon ox(\lambda)(Cox(t) + \Delta Cox(t)) + \epsilon deox(\lambda)(Cdeox(t) + \Delta Cdeox(t))]I0(t) \quad (6)$$

$$Id'(t) = Ds \cdot \exp[-[\epsilon ox(\lambda)Cox(t) + \epsilon deox(\lambda)Cdeox(t)]d]I0(t) \quad (7)$$

Next, equations (6) and (7) are expressed in terms of natural logarithm and then equation (7) is subtracted from equation (6) to obtain the following equation (8). The left side of equation (8) is the measured logarithmic difference signal.

$$\ln[Id(t)/Id'(t)] = -[\epsilon ox(\lambda)\Delta Cox(t) + \epsilon deox(\lambda)\Delta Cdeox(t)]d \quad (8)$$

Here, when 805 nm±10 nm is particularly used as the light source wavelength for measurement, $$\epsilon ox(805\pm10) \lesssim \epsilon deox(805\pm10) \quad (9)$$

stands and by using constant K, equation (8) can be reduced to $$\ln[Id(t)/Id'(t)] = -[\Delta Cox(t) + \Delta Cdeox(t)] \cdot K \quad (10)$$

Accordingly, the logarithmic difference signal measured by using the light source wavelength 805 nm±10 nm represents a value corresponding to a change amount in hemodynamic amount [ΔCox(t)+ΔCdeox(t)] (hereinafter referred to as relative hemodynamic change amount). Also, when the number of wavelengths used for the light source is set to two (λ1,λ2), different intensity modulation frequencies (f1,f2) are applied to the respective wavelengths and frequency separation is effected by means of the lock-in amplifiers, transmitting light intensity signals of the individual wavelengths can be measured. Accordingly, equation (8) holds for the respective wavelengths and a simultaneous equation consisting of the following equations (11) and (12) can be introduced:

$$\ln[Id(\lambda1,t)/Id'(\lambda1,t)] \quad (11)$$
$$= -[\epsilon ox(\lambda1)\Delta Cox(t) + \epsilon deox(\lambda1)\Delta Cdeox(t)]d$$

$$\ln[Id(\lambda2,t)/Id'(\lambda2,t)] \quad (12)$$
$$= -[\epsilon ox(\lambda2)\Delta Cox(t) + \epsilon deox(\lambda2)\Delta Cdeox(t)]d$$

Since the extinction coefficients ϵox(λ1), ϵox(λ2), ϵdeox (λ1) and ϵdeox(λ2) are known, value ΔCox(t)d corresponding to a change amount of hemoglobin oxide and value ΔCdeox(t) corresponding to a change amount of reduced hemoglobin can be determined by solving equations (11) and (12) with the computer 213 and time series data representative of a determined relative change amount can be displayed graphically on the display unit 214. For expansion of the above, the number of wavelengths can be increased, d can be erased or a relative change amount of concentration of a light absorbing substance, other than hemoglobin, which exists in a small amount can be determined.

Figure 16:
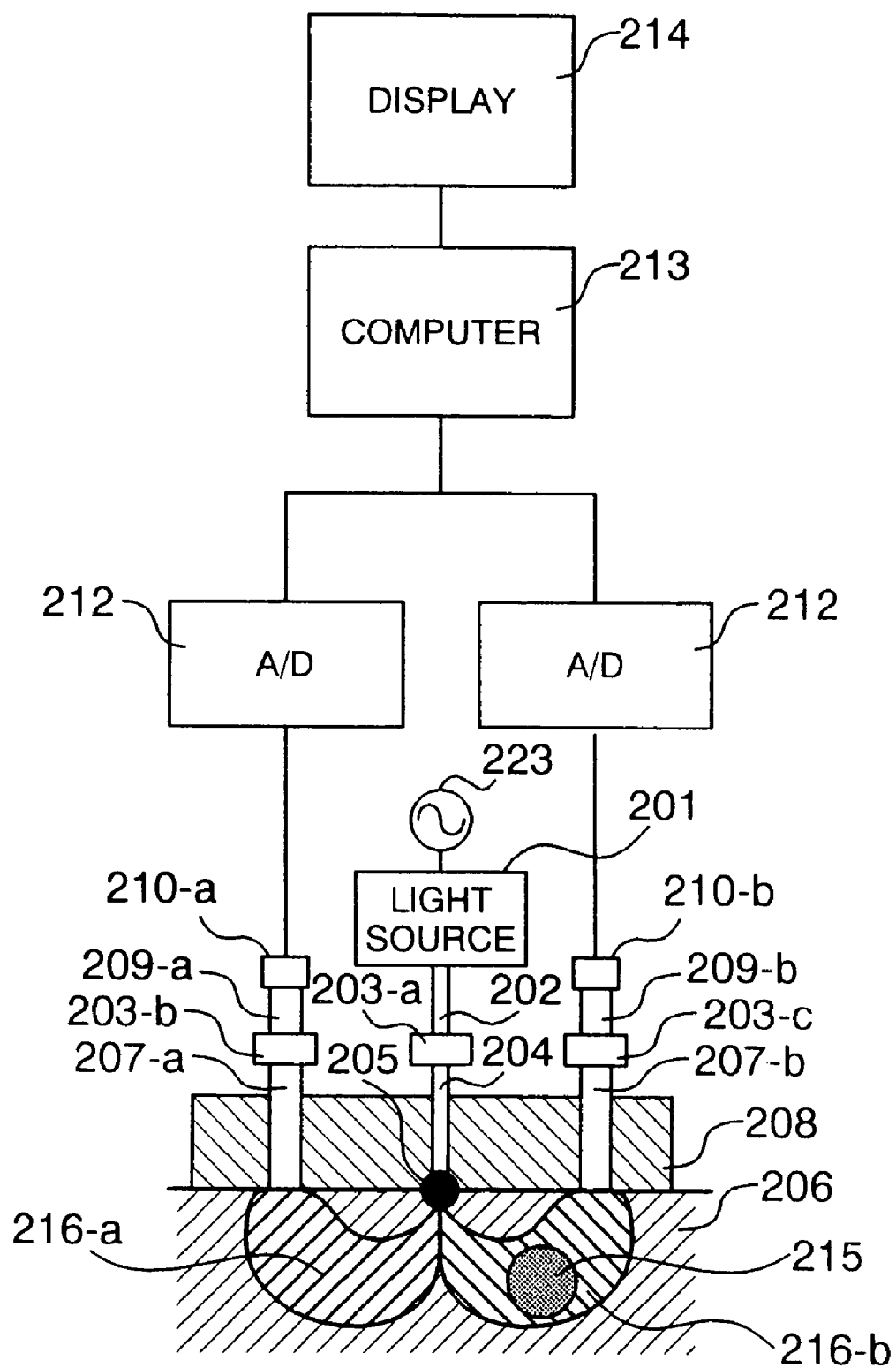
FIG. 16 is a block diagram for explaining the construction of a system according to another embodiment of the present invention.

Alternatively, as shown in FIG. 16, the lock-in amplifiers, logarithmic amplifiers and differential amplifiers may not be used, detection signals from the photodetectors 210a and 210b may be converted into digital signals by A/D converters 212, respectively, the digital signals may then be FFT processed with the computer 213 to extract only a signal corresponding to the intensity modulation frequency of the light source, a logarithmic difference between transmitting light intensity levels at two different detection positions is calculated through a similar procedure to the above calculation process, and the determined relative change amount can be displayed graphically as time series data on the display unit 214.

Figure 17A:
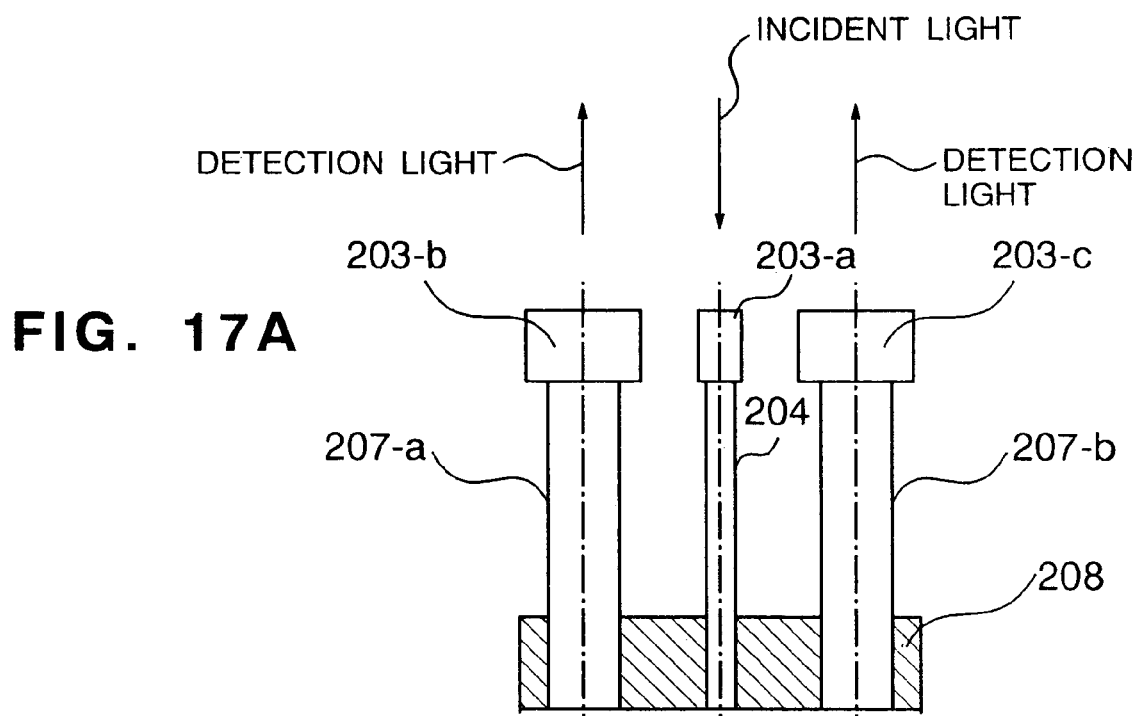
FIGS. 17A and 17B are schematic sectional and bottom views of a light detection probe in another embodiment of the present invention.
Figure 17B:
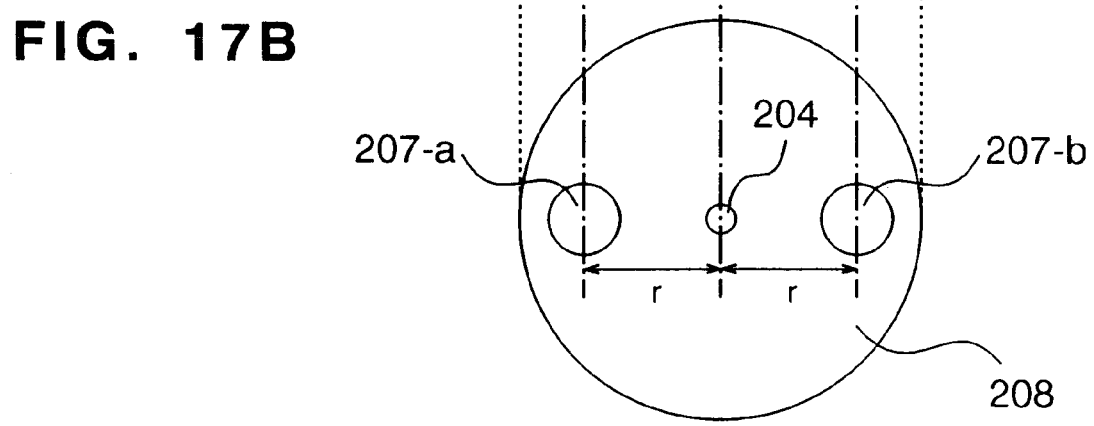

FIGS. 17A and 17B show an example of the light detection probe. FIG. 17A illustrates a section of the light detection probe and FIG. 17B is a diagram of the light detection probe as viewed from a subject contact surface.

The light detection probe is comprised of the single light irradiation optical fiber 204, the two light detection optical fibers 207a and 207b and the optical fiber fixing member 208 having its surface painted in black and made of metal or plastics, and the optical fibers are connected with the optical fiber couplers 203a, 203b and 203c. In order to maintain flexibility of the individual optical fibers, each optical fiber is constructed of a plurality of optical fibers. As a material of the optical fiber, plastics or quartz is used. When the present light detection probe is used for a living body, the subject contact surface 217 is covered with, for example, resilient sponge.

The size of the detection surface of each light detection optical fibers 207a or 207b must be changed in accordance with the purpose and the state of a subject but when measurement of, for example, the cerebral function is performed, the sectional shape is made to be a circle having a diameter of about 1 mm to 20 mm or a square having a side of about 1 mm to 20 mm. The two light detection optical fibers 207a and 207b are disposed at positions r (r=5 mm to 50 mm) distant from the light irradiation optical fiber 204 and here, disposed symmetrically. A plurality of kinds of light detection probes, in which the distance r differs and the sectional shape of each light detection optical fiber 207a or 207b differs, are prepared and one probe is exchanged with another in compliance with the purpose of measurement, thereby permitting convenient measurement. Since the light reaching depth substantially equals the distance r from the light source, a depth approximating the cerebral cortex of the cerebrum can be measured from the head surface through the skull.

Figure 18:
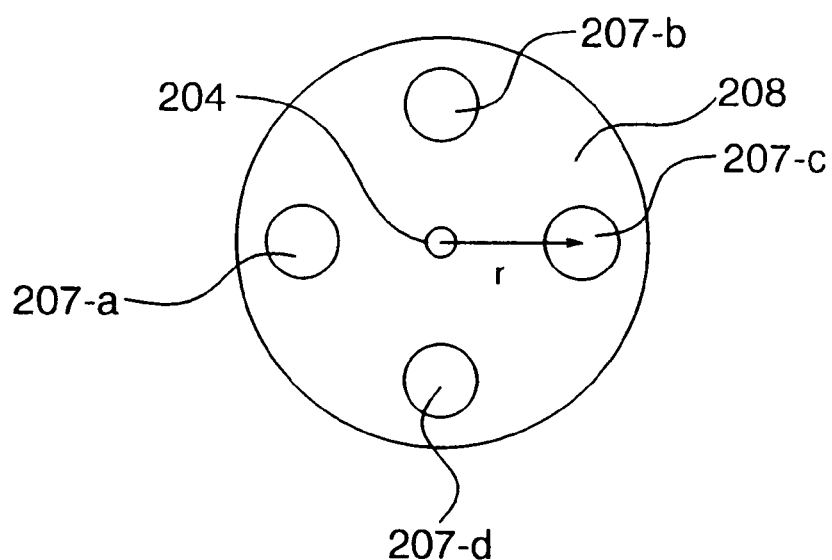
FIG. 18 is a schematic bottom view showing another embodiment of the light detection probe.

In the light detection probe, various forms of disposition of the light detection optical fibers 207 can be conceivable. For example, as shown in FIG. 18, four light detection optical fibers 207a, 207b, 207c and 207d can be disposed at positions r equidistant from the light irradiation optical fiber 204, and desired two light detection optical fibers can be selected for measurement. In an alternative, any optical fiber may not be used but a lens system may be used or a light source and photodetectors can be disposed directly in the fixing member 208.

Figure 19:
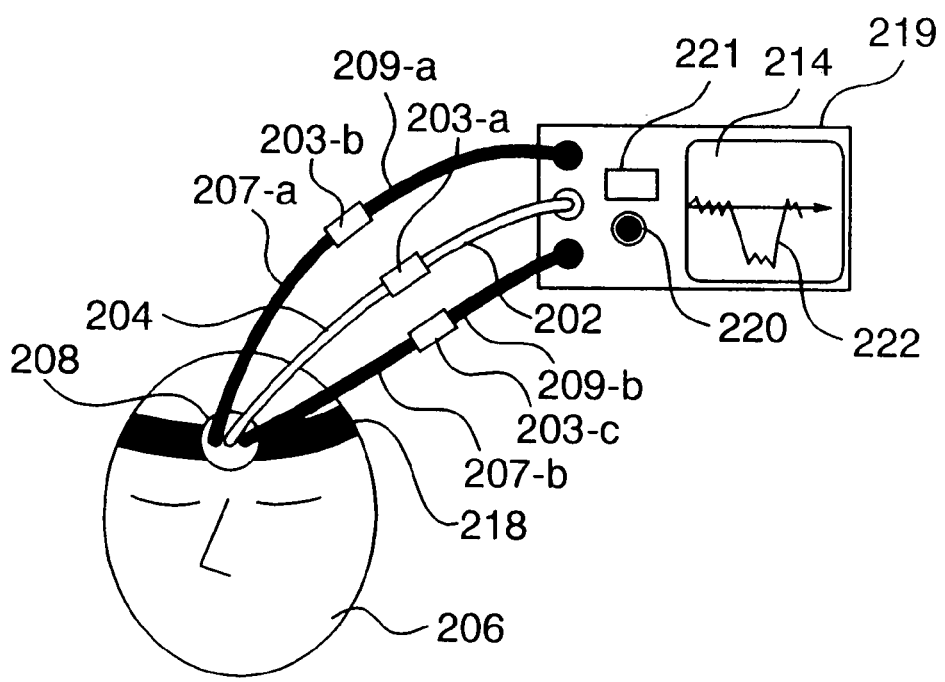
FIG. 19 is a schematic diagram for explaining an example of use of the light detection probe.

FIG. 19 shows an example where the optical measuring system according to the present invention is used for measurement of the cerebrum of a living body. A light detection probe comprised of optical fiber couplers 203a, 203b and 203c, a light irradiation optical fiber 204, light detection optical fibers 207a and 207b, and an optical fiber fixing member 208 is fixed to a subject 206 by means of a fitting belt 218 made of rubber. The light irradiation optical fiber 204 is connected to a light source optical fiber 202 through the optical fiber coupler 203a and the light detection optical fibers 207a and 207b are connected to optical fibers 209a and 209b for light detection, respectively, through the optical fiber couplers 203b and 203c. Provided on a front panel of the optical measuring system 219 are connectors for the light source optical fiber 202 and light detection optical fibers 209a and 209b, an output signal adjusting knob 220, an output signal value indicating window 221 and a display unit 214. Arranged in the optical measuring system 219 are the differential amplifiers, A/D converters, microprocessor, light source, photodetectors, optical switches and other necessary electric circuits.

A logarithmic difference signal value between transmitting light intensity levels detected at two sites is digitally indicated on the output signal value indicating window 221 and an offset value of the logarithmic difference signal value is determined using the output signal adjusting knob 220. For example, in the absence of a local change in hemodynamic movement in the cerebrum of the subject, the logarithmic difference signal between transmitting light intensity levels detected at the two sites is so adjusted as to be zero. Thereafter, measurement is started and time series data 222 representative of the logarithmic difference signal is graphically displayed on the display unit 214. Also, the arithmetic operation described previously is carried out to graphically display a local hemodynamic amount or time-variable changes in relative change amounts of hemoglobin oxide quantity and reduced hemoglobin quantity.

Embodiment 4

Figure 20:
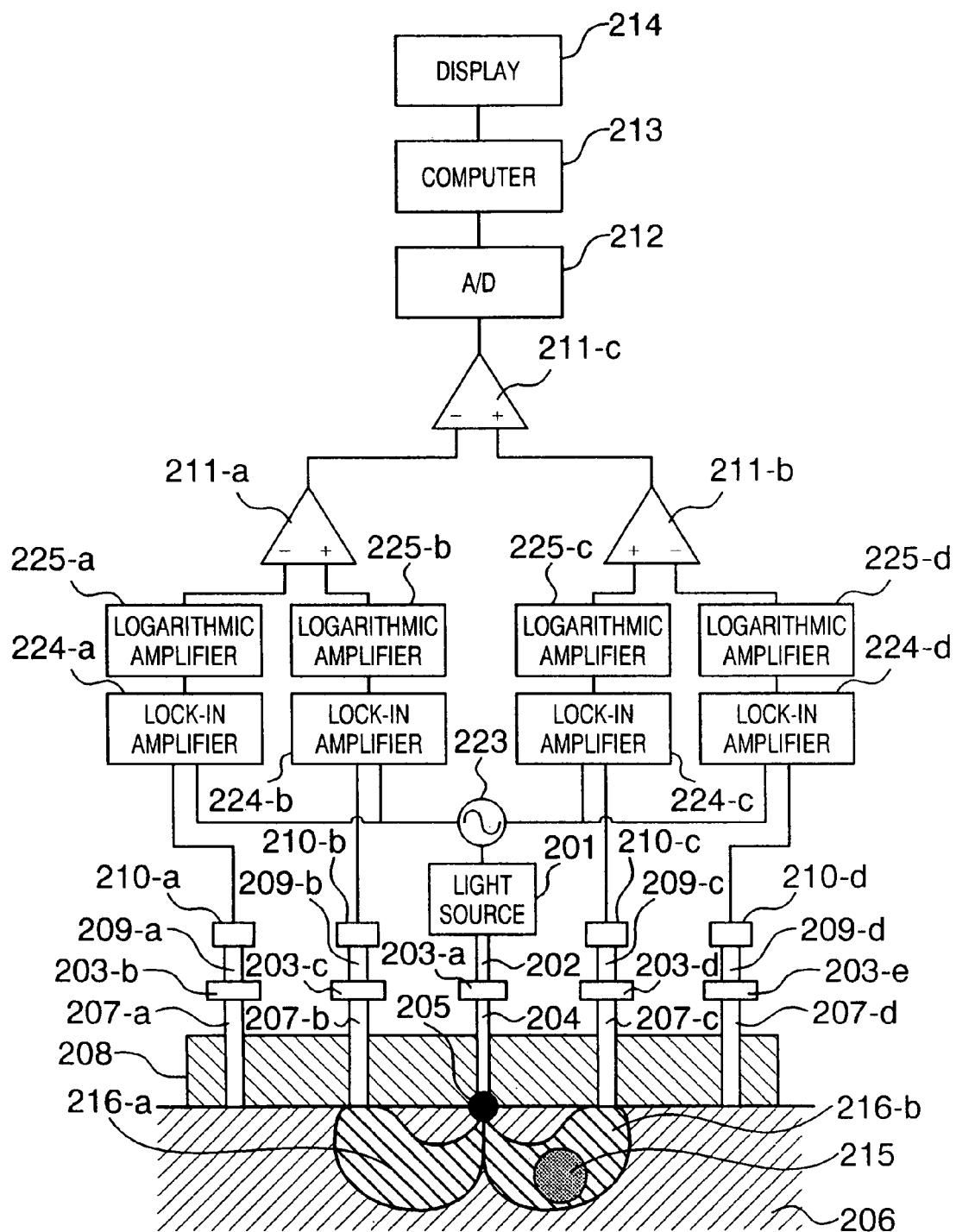
FIG. 20 is a block for explaining the construction of a system according to another embodiment of the present invention.

The schematic construction of embodiment 4 of the living body optical measurement system according to the present invention is shown in FIG. 20.

Light emitted from a light source 201 is collected using a lens system so as to impinge on an optical fiber 202 for light source. The light emitted from the light source is modulated in intensity with a desired frequency of about 100 Hz to 10 MHz by means of an oscillator 223 in order to remove noises due to external disturbance. Since the light source optical fiber 202 is connected to an optical fiber 204 for light irradiation through an optical fiber coupler 203a, the light from the light source is transmitted to the light irradiation optical fiber 204 and is irradiated on a subject 206 by way of a light irradiation position 205. The wavelength of the light used depends on spectroscopic characteristics of an in vivo substance of interest but when the oxygen saturation amount and the blood amount are measured from concentration values of Hb and HbO2, a single or a plurality of wavelengths can be selected, for use, from light having the wavelength range of from 600 nm to 1400 nm. A semiconductor laser, a titanium/sapphire laser or a light emitting diode can be used as the light source.

Four light detection optical fibers 207a, 207b, 207c and 207d for detecting light transmitting through the subject 206 and going out of it are disposed at four different sites on the subject 206. In the present embodiment, the two light detection optical fibers 207b and 207c are disposed at two sites which are point symmetrical to a symmetry center of the light irradiation position 205, the light detection optical fiber 207a is disposed such that the centroid point of the light detection optical fiber 207a is on a half-line having its origin at the centroid point of the light irradiation position and passing through the centroid point of the light detection optical fiber 207b, and the light detection optical fiber 207d is disposed such that the centroid point of the light detection optical fiber 207d is on a half-line having its origin at the centroid point of the light irradiation position and passing through the centroid point of the light detection optical fiber 207c. The light detection optical fibers 207a and 207d can be disposed anywhere so long as their centroid points are on the half-lines but in the present embodiment, they are disposed point-symmetrically to the symmetry center of the light irradiation position 205 and outside the light detection optical fibers 207b and 207c. Here, the light irradiation optical fiber 204 and the light detection optical fibers 207a, 207b, 207c and 207d are held in place by means of an optical fiber fixing member 208 made of metal and having its surface painted in black. Since the light detection optical fibers 207a, 207b, 207c and 207d are connected to optical fibers 209a, 209b, 209c and 209d for photodetectors through optical fiber couplers 203b, 203c, 203d and 203e, transmitting light rays detected by the light detection optical fibers 207a, 207b, 207c and 207d are transmitted to photodetectors 210a, 210b, 210c and 210d and subjected to photoelectric conversion by the photodetectors 210, so that transmitting light intensity levels subject to the photoelectric conversion are delivered in the form of electric signal intensity levels. Used as the photodetectors 210 are photoelectric conversion elements such as for example photodiodes or photomultiplier tubes.

Of electric signals indicative of transmitting light intensity levels delivered out of the photodetectors 210a and 210b, only frequency components for intensity modulation of the light source are extracted by lock-in amplifiers 224a and 224b, respectively. While an output from the lock-in amplifier 224a is subjected to logarithmic conversion by a logarithmic amplifier 225a and then inputted to the negative pole of a differential amplifier 211a, an output from the lock-in amplifier 224b is subjected to logarithmic conversion by a logarithmic amplifier 225b and subsequently inputted to the positive pole of the differential amplifier 0.211a. Of electric signals indicative of transmitting light intensity levels delivered out of the photodetectors 210c and 210d, only frequency components for intensity modulation of the light source are extracted by lock-in amplifiers 224c and 224d, respectively. While an output from the lock-in amplifier 224d is subjected to logarithmic conversion by a logarithmic amplifier 225d and then inputted to the negative pole of a differential amplifier 211b, an output from the lock-in amplifier 224c is subjected to logarithmic conversion by a logarithmic amplifier 225c and subsequently inputted to the positive pole of the differential amplifier 211b. Further, an output from the differential amplifier 211a is inputted to the negative pole of a differential amplifier 211c and an output from the differential amplifier 211b is inputted to the positive pole of the differential amplifier 211c. As a result, a difference signal among transmitting light intensity levels at the four different sites is delivered out of the differential amplifier 211c as an output signal. The output signal from the differential amplifier 211c is sequentially converted into a digital signal by an A/D converter 212, fetched into a computer 213 and displayed graphically on a display unit 214 as time series data.

Here, when a region 215 where the hemodynamic movement changes locally is included in only a view field 216b of the light detection optical fiber as shown in FIG. 20, the logarithmic differential signal of transmitting light intensity delivered out of the differential amplifier 211c reflects only a change in local hemodynamic movement. On the presupposition that for near infrared rays, hemoglobin serving as a main constituent in hemodynamic dominantly acts on extinction, the meaning of the logarithmic difference signal delivered out of the differential amplifier 211c will be described below.

Where measuring time is t, light source wavelength is $\lambda$, irradiation light intensity is $I0(t)$, concentration values of hemoglobin oxide and reduced hemoglobin are $Cox(t)$ and $Cdeox(t)$, respectively, changes in concentration values of hemoglobin oxide and reduced hemoglobin which occur at the local region 215 are $\Delta Cox(t)$ and $\Delta Cdeox(t)$, respectively, extinction coefficients for light source wavelength $\lambda$ of hemoglobin oxide and reduced hemoglobin are $\epsilon ox(\lambda)$ and $\epsilon deox(\lambda)$, respectively, attenuation contained in transmitting light intensity levels detected by the photodetectors 210b and 210c and due to scattering and absorption caused by other constituents than hemoglobin is Ds1, attenuation contained in transmitting light intensity levels detected by the photodetectors 210a and 210d and due to scattering and absorption caused by other constituents than hemoglobin is Ds2, weight coefficient contained in the transmitting light intensity levels detected by the photodetectors 210b and 210c and caused by scattering is d1, and weight coefficient contained in the transmitting light intensity levels detected by the photodetectors 210a and 210d and caused by scattering is d2, transmitting light intensity signal $Id1(t)$ detected by the photodetector 210c, transmitting light intensity signal $Id2(t)$ detected by the photodetector 210d, transmitting light intensity signal $Id1'(t)$ detected by the photodetector 210b and transmitting light intensity signal $Id2'(t)$ detected by the photodetector 210a are given by the following equations (13) to (16):

$$Id1(t) = Ds1 \cdot \exp[-[\epsilon ox(\lambda)(Cox(t) + \Delta Cox(t)) + \epsilon deox(\lambda)(Cdeox(t) + \Delta Cdeox(t))]d1]I0(t) \quad (13)$$

$$Id2(t) = Ds2 \cdot \exp[-[\epsilon ox(\lambda)(Cox(t) + \Delta Cox(t)) + \epsilon deox(\lambda)(Cdeox(t) + \Delta Cdeox(t))]d2]I0(t) \quad (14)$$

$$Id1'(t) = Ds1 \cdot \exp[-[\epsilon ox(\lambda)Cox(t) + \epsilon deox(\lambda)Cdeox(t)]d1]I0(t) \quad (15)$$

$$Id2'(t) = Ds2 \cdot \exp[-[\epsilon ox(\lambda)Cox(t) + \epsilon deox(\lambda)Cdeox(t)]d2]I0(t) \quad (16)$$

Next, equations (13) and (14) are expressed in terms of natural logarithm and then equation (14) is subtracted from equation (13) to obtain the following equation (17):

$$\ln[Id1(t)/Id2(t)] = \ln[Ds1/Ds2] - [\epsilon ox(\lambda)(Cox(t) + \Delta Cox(t)) + \epsilon deox(\lambda)(Cdeox(t) + \Delta Cdeox(t))](d1 - d2) \quad (17)$$

Equations (15) and (16) are expressed in terms of natural logarithm and then equation (16) is subtracted from equation (15) to obtain the following equation (18):

$$\ln[Id1'(t)/Id2'(t)] = \ln[Ds1/Ds2] - [\epsilon ox(\lambda)(Cox(t) + \Delta Cox(t)) + \epsilon deox(\lambda)(Cdeox(t) + \Delta Cdeox(t))](d1 - d2) \quad (18)$$

The left side of equation (17) represents the output of the differential amplifier 211b and the left side of equation (18) represents the output of the differential amplifier 211a. Here, by subtracting equation (18) from equation (17), the following equation (19) is obtained:

$$\ln[(Id1(t)/Id2(t))(Id2'(t)/Id1'(t)] = \quad (19)$$
$$-[\in ox(\lambda)\Delta Cox(t) + \in deox(\lambda)\Delta Cdeox(t)](d1-d2)$$

The left side of equation (19) represents the output of the differential amplifier 211c, that is, the measured logarithmic difference signal.

Here, when 805 nm±10 nm is particularly used as the light source wavelength for measurement, the aforementioned relation of equation (9) stands and by using constant K, equation (19) can be reduced to the following equation (20):

$$\ln[(Id1(t)/Id2(t))(Id2'(t)/Id1'(t))] = \quad (20)$$
$$-[\Delta Cox(t) + \Delta Cdeox(t)] \cdot K$$

Accordingly, the logarithmic difference signal measured using the light source wavelength 805 nm±10 nm represents a value corresponding to a relative hemodynamic change amount [$\Delta Cox(t)+\Delta Cdeox(t)$].

Also, when the number of wavelengths used for the light source is two ($\lambda 1, \lambda 2$), different intensity modulation frequencies (f1,f2) are applied to the respective wavelengths and frequency separation is effected by means of the lock-in amplifiers, transmitting light intensity signals of the individual wavelengths can be measured. Accordingly, equation (19) holds for the respective wavelengths and a simultaneous equation consisting of the following equations (21) and (22) can be introduced:

$$\ln[(Id1(\lambda 1, t)/Id2(\lambda 1, t))(Id2'(\lambda 1, t)/Id1'(\lambda 1, t))] = \quad (21)$$
$$-[\in ox(\lambda 1)\Delta Cox(t) + \in deox(\lambda 1)\Delta Cdeox(t)](d1-d2)$$
$$\ln[(Id1(\lambda 2, t)/Id2(\lambda 2, t))(Id2'(\lambda 2, t)/Id1'(\lambda 2, t))] = \quad (22)$$
$$-[\in ox(\lambda 2)\Delta Cox(t) + \in deox(\lambda 2)\Delta Cdeox(t)](d1-d2)$$

Since the extinction coefficients $\epsilon ox(\lambda 1)$, $\epsilon ox(\lambda 2)$, $\epsilon deox(\lambda 1)$ and $\epsilon deox(\lambda 2)$ are known, value $\Delta Cox(t)(d1-d2)$ corresponding to a change amount of hemoglobin oxide and value $\Delta Cdeox(t)(d1-d2)$ corresponding to a change amount of reduced hemoglobin can be determined by solving equations (21) and (22) with the computer 213 and time series data representative of a determined relative change amount can be displayed graphically on the display unit 214. For expansion of the above, the number of wavelengths can be increased, (d1−d2) can be erased or a relative change amount of concentration of a light absorbing substance, other than hemoglobin, which exists in a small amount can be determined.

Figure 21:
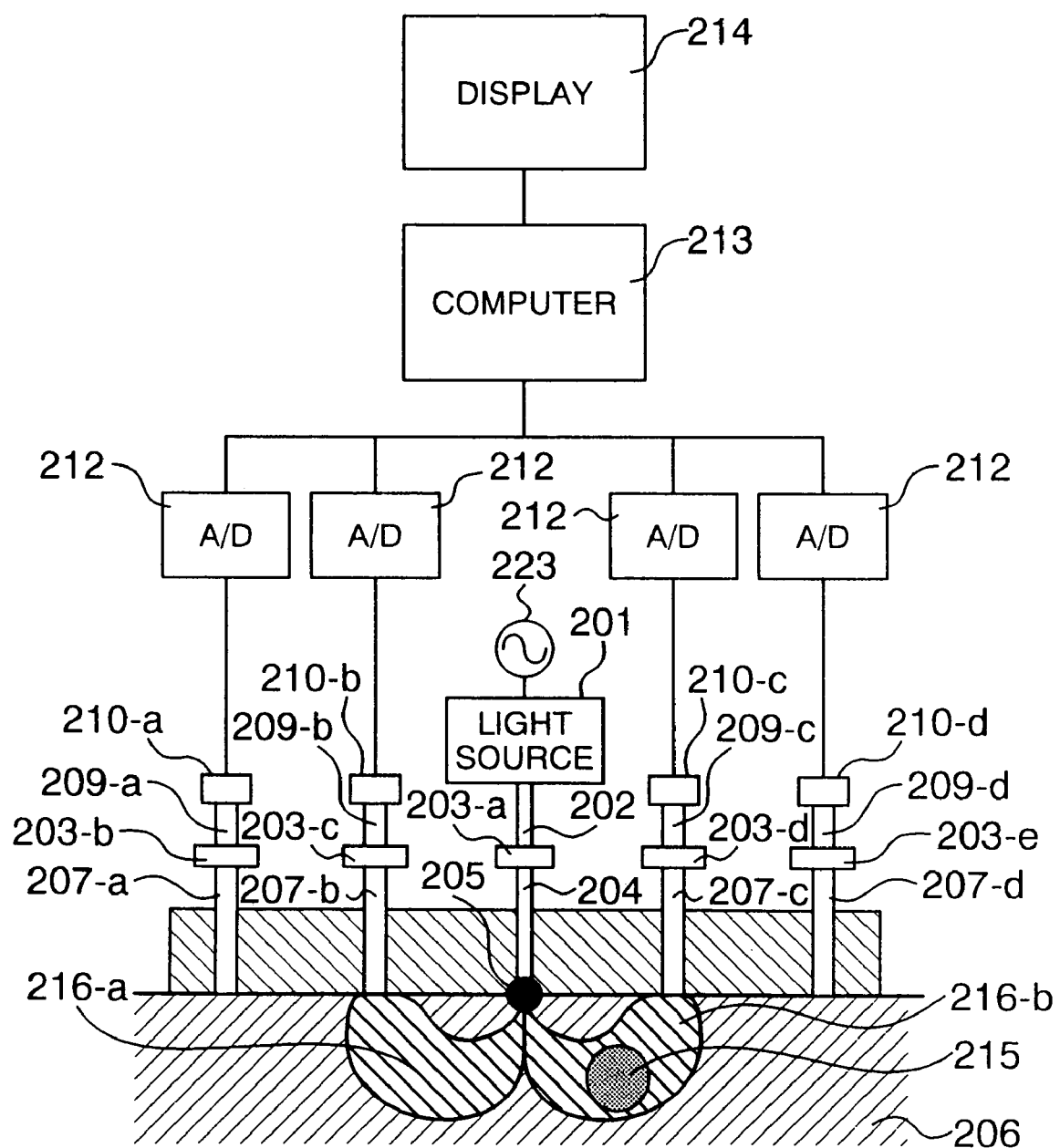
FIG. 21 is a block for explaining the construction of a system according to another embodiment of the present invention.

Alternatively, as shown in FIG. 21, the lock-in amplifiers, logarithmic amplifiers and differential amplifiers may not be used, detection signals from the photodetectors 210a, 210b, 210c and 210d may be converted into digital signals by the A/D converters 212, respectively, the digital signals may then be FFT processed with the computer 213 to extract only a signal corresponding to the intensity modulation frequency of the light source, a logarithmic difference among transmitting light intensity levels at four different detection positions may be calculated through a similar procedure to the above calculation process, and then the determined relative change amount can be displayed graphically as time series data on the display unit 214.

Embodiment 5

Figure 22:
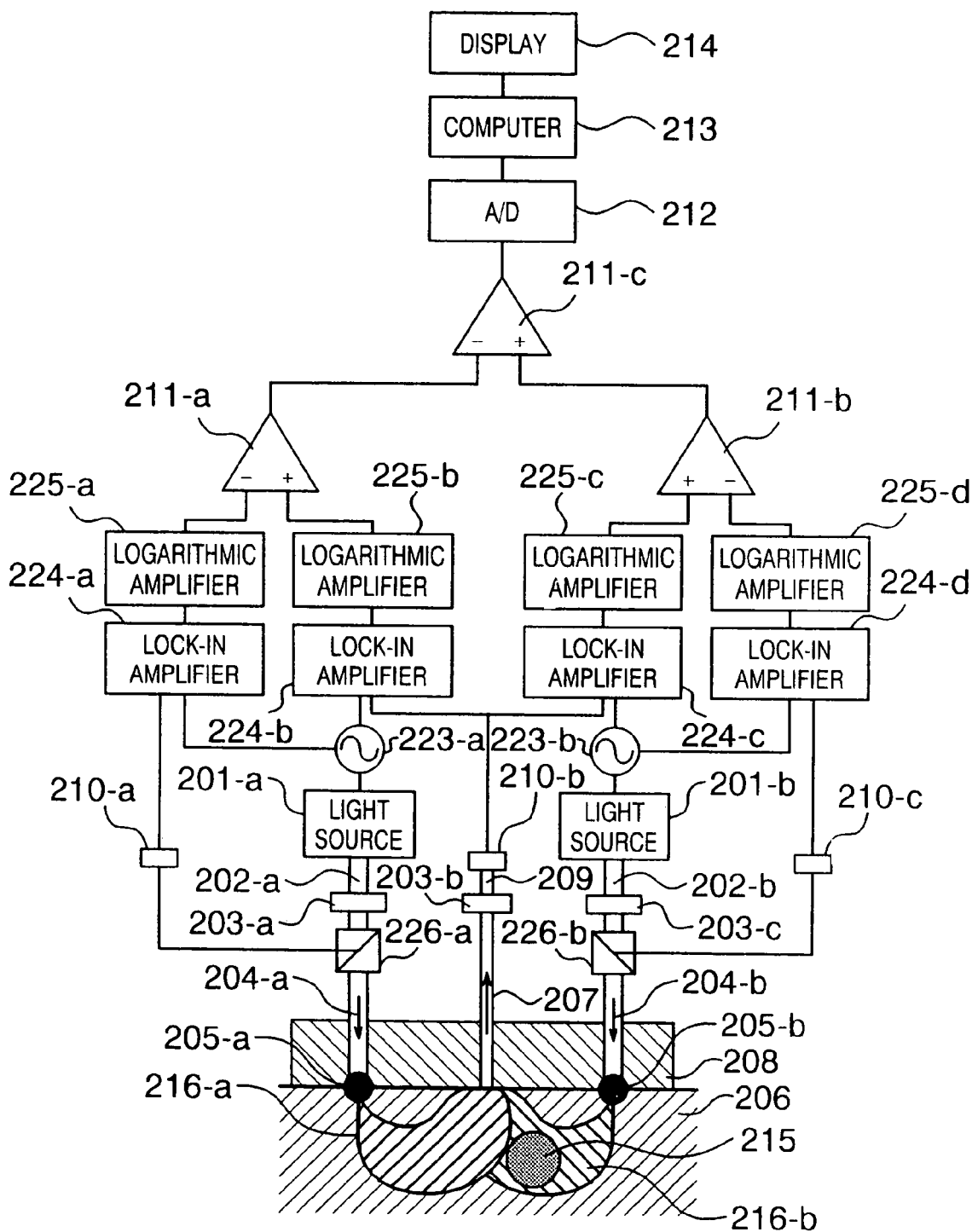
FIG. 22 is block for explaining the construction of a system according to another embodiment of the present invention.

The schematic construction of embodiment 5 of the living body optical measurement system according to the present invention is shown in FIG. 22.

Light rays emitted from light sources 201a and 201b are collected using lens systems so as to impinge on an optical fiber 202a for light source and an optical fiber 202b for light source, respectively. The light rays emitted from the respective light sources are modulated in intensity with desired different frequencies f of about 100 Hz to 10 MHz by means of oscillators 223a and 223b in order to remove noises due to external disturbance. Here, the intensity modulation frequency for the light source 201a is set to f1 and the intensity modulation frequency for the light source 201b is set to f2. Since the light source optical fiber 202a is connected to an optical fiber 204a for light irradiation through an optical fiber coupler 203a and the light source optical fiber 202b is connected to an optical fiber 204b for light irradiation through an optical fiber coupler 203c, the light rays from the respective light sources are transmitted to the light irradiation optical fibers 204a and 204b and irradiated on a subject 206 by way of light irradiation positions 205a and 205b. In order to obtain reference light rays, the light is split at a halfway point of each of the light irradiation optical fibers 204a and 204b by means of a splitter 226a or 226b and the intensity of each light source is converted into an electric signal by means of a photodetector 210a or 210c. A reference light intensity signal for the light source 201a, delivered out of the photodetector 210a, is inputted to a lock-in amplifier 224a and separated on the basis of a reference frequency from the oscillator 223a. An output of the lock-in amplifier 224a is inputted to a logarithmic amplifier 225a so as to undergo logarithmic conversion and then inputted to the negative pole of a differential amplifier 211a. A reference light intensity signal for the light source 201b, delivered out of the photodetector 210c, is inputted to a lock-in amplifier 224d and separated on the basis of a reference frequency from the oscillator 223b. An output of the lock-in amplifier 224d is inputted to a logarithmic amplifier 225d so as to undergo logarithmic conversion and then inputted to the negative pole of a differential amplifier 211b. The wavelength of the light used depends on spectroscopic characteristics of an in vivo substance of interest but when the oxygen saturation amount and the hemodynamic amount are measured from concentration values of Hb and HbO2, a single or a plurality of wavelengths can be selected, for use, from light having the wavelength range of from 600 nm to 1400 nm. A semiconductor laser, a titanium/sapphire laser or a light emitting diode can be used as the light source.

For detection of light transmitting through a subject 206 and going out of it, one optical fiber 207 for light detection is disposed at a position on the subject 206 which is equidistant from light irradiation positions 205a and 205b. Here, the light irradiation optical fibers 204a and 204b and the light detection optical fiber 207 are held in place by means of an optical fiber fixing member 208 having its surface painted in black. Since the light detection optical fiber 207 is connected to an optical fiber 209 for light detection through an optical fiber coupler 203b, transmitting light detected by the light detection optical fiber 207 is transmitted to a photodetector 210b and subjected to photoelectric conversion by the photodetector 210b, so that the transmitting light intensity is delivered in the form of electrical signal intensity. Used as the photodetector 210b is a photoelectric conversion element such as for example a photodiode or a photomultiplier tube.

Since the electric signal representative of the transmitting light intensity level delivered out of the photodetector 210b contains the transmitting light intensity signal for the light source 201a and the transmitting light intensity signal for the light source 201b, only an intensity modulation frequency component for the light source 201a is extracted by a lock-in amplifier 224b and only an intensity modulation frequency component signal for the light source 201b is extracted by a lock-in amplifier 224c. An output from the lock-in amplifier 224b is subjected to logarithmic conversion by a logarithmic amplifier 225b and then inputted to the positive pole of the differential amplifier 211a. An output from the lock-in amplifier 224c is subjected to logarithmic conversion by a logarithmic amplifier 225c and subsequently inputted to the positive pole of the differential amplifier 211b. As a result, a logarithmic difference signal between the intensity of the light source 201a and the transmitting light intensity for the light source 201a is delivered out of the differential amplifier 211a as an output signal, and a logarithmic difference signal between the intensity of the light source 201b and the transmitting light intensity for the light source 201b is delivered out of the differential amplifier 211b as an output signal. Further, an output from the differential amplifier 211a is inputted to the negative pole of a differential amplifier 211c and an output from the differential amplifier 211b is inputted to the positive pole of the differential amplifier 211c, so that a logarithmic differential signal between transmitting light intensity levels which is removed of fluctuation in the light source intensity can be delivered out of the differential amplifier 211c. The output signal from the differential amplifier 211c is sequentially converted into a digital signal by an A/D converter 212, fetched into a computer 213 and displayed on a display unit 214 as time series data.

Here, when a region 215 where the hemodynamic movement changes locally is included in only a view field 216b of the light detection optical fiber as shown in FIG. 22, the measured logarithmic differential signal reflects only a change in local hemodynamic movement. On the presupposition that for near infrared rays, hemoglobin serving as a main constituent in hemodynamic dominantly acts on extinction, the meaning of the measured logarithmic difference signal will be described below.

Where measuring time is t, light source wavelength is λ, irradiation light intensity from the irradiation position 205b is I0(t), irradiation light intensity from the irradiation position 205a is I0'(t), reference light intensity from the splitter 226b is Ir(t), reference light intensity from the splitter 226b is Ir'(t), ratio of splitting to reference light of the splitter is α indicating that $$I0(t):Ir(t)=I0'(t):Ir'(t)=1:\alpha,$$

concentration values of hemoglobin oxide and reduced hemoglobin are Cox(t) and Cdeox(t), respectively, changes in concentration values of hemoglobin oxide and reduced hemoglobin which occur at the local region 215 are ΔCox(t) and ΔCdeox, respectively, extinction coefficients for light source wavelength λ of hemoglobin oxide and reduced hemoglobin are ϵox(λ) and ϵdeox(λ), respectively, attenuation due to scattering and absorption caused by other constituents than hemoglobin is Ds, and weight coefficient caused by scattering is d, transmitting light intensity signal Id(t) for the light source 201b detected by the photodetector 210b, that is, the output from the lock-in amplifier 224c is given by the following equation (23) and transmitting light intensity signal Id'(t) for the light source 201a, that is, the output from the lock-in amplifier 224b is given by the following equation (24):

$$Id(t) = Ds \cdot \exp[-[\in ox(\lambda)(Cox(t) + \Delta Cox(t) + \quad (23)$$
$$\in deox(\lambda)(Cdeox(t) + \Delta Cdeox(t))]d]I0(t)$$

$$Id'(t) = Ds \cdot \exp[-[\in ox(\lambda)Cox(t) + \quad (24)$$
$$\in deox(\lambda)(Cdeox(t)]d]I0'(t)$$

Next, equations (23) and (24) are expressed in terms of natural logarithm and then equation (23) is reduced to the following equation (25) and equation (24) is reduced to the following equation (26):

$$\ln[Id(t)/I0(t)] = \ln[Ds] - \quad (25)$$
$$[\in ox(\lambda)(Cox(t) + \Delta Cox(t) + $$
$$\in deox(\lambda)(Cdeox(t) + \Delta Cdeox(t))]d$$

$$\ln[Id'(t)/I0'(t)] = \ln[Ds] - \quad (26)$$
$$[\in ox(\lambda)(Cox(t) + $$
$$\in deox(\lambda)(Cdeox(t)]d$$

Further, equation (26) is subtracted from equation (25) to obtain the following equation (27):

$$\ln[(Id(t)/Id'(t))(I0'(t)/I0(t))] = -[\in ox(\lambda)\Delta Cox(t) + \quad (27)$$
$$\in deox(\lambda)\Delta Cdeox(t)]d$$

Here, $$Ir(t) = \alpha I0(t) \quad (28)$$
$$Ir'(t) = \alpha I0'(t) \quad (29)$$

stand and therefore, the output from the differential amplifier 211a is $$\ln[Id'(t)/\alpha I0'(t)]$$

and the output from the differential amplifier 211c is $$\ln[(Id(t)/Id'(t))(I0'(t)/I0(t))] \quad (30)$$

Since equation (30) equals the left side of equation (27), the logarithmic difference signal delivered out of the differential amplifier 211c is equivalent to equation (27).

Here, when 805 nm±10 nm is particularly used as the light source wavelength for measurement, the aforementioned relation of equation (9) stands and by using constant K, equation (27) can be reduced to the following equation (31):

$$\ln[(Id(t)/Id'(t))(I0'(t)/I0(t))] = -[\Delta Cox(t) + \Delta Cdeox(t)]K \quad (31)$$

Accordingly, the logarithmic difference signal measured using the light source wavelength 805 nm±10 nm represents a value corresponding to a relative hemodynamic change amount [ΔCox(t)+ΔCdeox(t)]·K. Also, when the number of wavelengths used for the light source is two (λ1,λ2), intensity modulation frequencies (f1, f2, f3, f4) which differ with the respective wavelengths and the respective irradiation positions are applied and frequency separation is effected by means of the lock-in amplifiers, transmitting light intensity signals for the individual wavelengths and the respective irradiation positions can be measured. Accordingly, equation (27) holds for the respective wavelengths and a simultaneous equation consisting of the following equations (32) and (33) can be introduced:

$$\ln[(Id(\lambda 1, t)/Id'(\lambda 1, t))(I0'(\lambda 1, t)/I0(\lambda 1, t))] = \quad (32)$$
$$-[\epsilon ox(\lambda 1)\Delta Cox(t) + \epsilon deox(\lambda 1)\Delta Cdeox(t)]d$$
$$\ln[(Id(\lambda 2, t)/Id'(\lambda 2, t))(I0'(\lambda 2, t)/I0(\lambda 2, t))] = \quad (33)$$
$$-[\epsilon ox(\lambda 2)\Delta Cox(t) + \epsilon deox(\lambda 2)\Delta Cdeox(t)]d$$

Since the extinction coefficients $\epsilon ox(\lambda 1)$, $\epsilon ox(\lambda 2)$, $\epsilon deox(\lambda 1)$ and $\epsilon deox(\lambda 2)$ are known, value $\Delta Cox(t)d$ corresponding to a change amount of hemoglobin oxide and $\Delta Cdeox(t)$ corresponding to a change amount of reduced hemoglobin can be determined by solving equations (32) and (33) with the computer 213 and time series data representative of a determined relative change amount can be displayed graphically on the display unit 214. For expansion of the above, the number of wavelengths can be increased, d can be erased or a relative change amount of concentration of a light absorbing substance, other than hemoglobin, which exists in a small amount can be determined.

Figure 23:
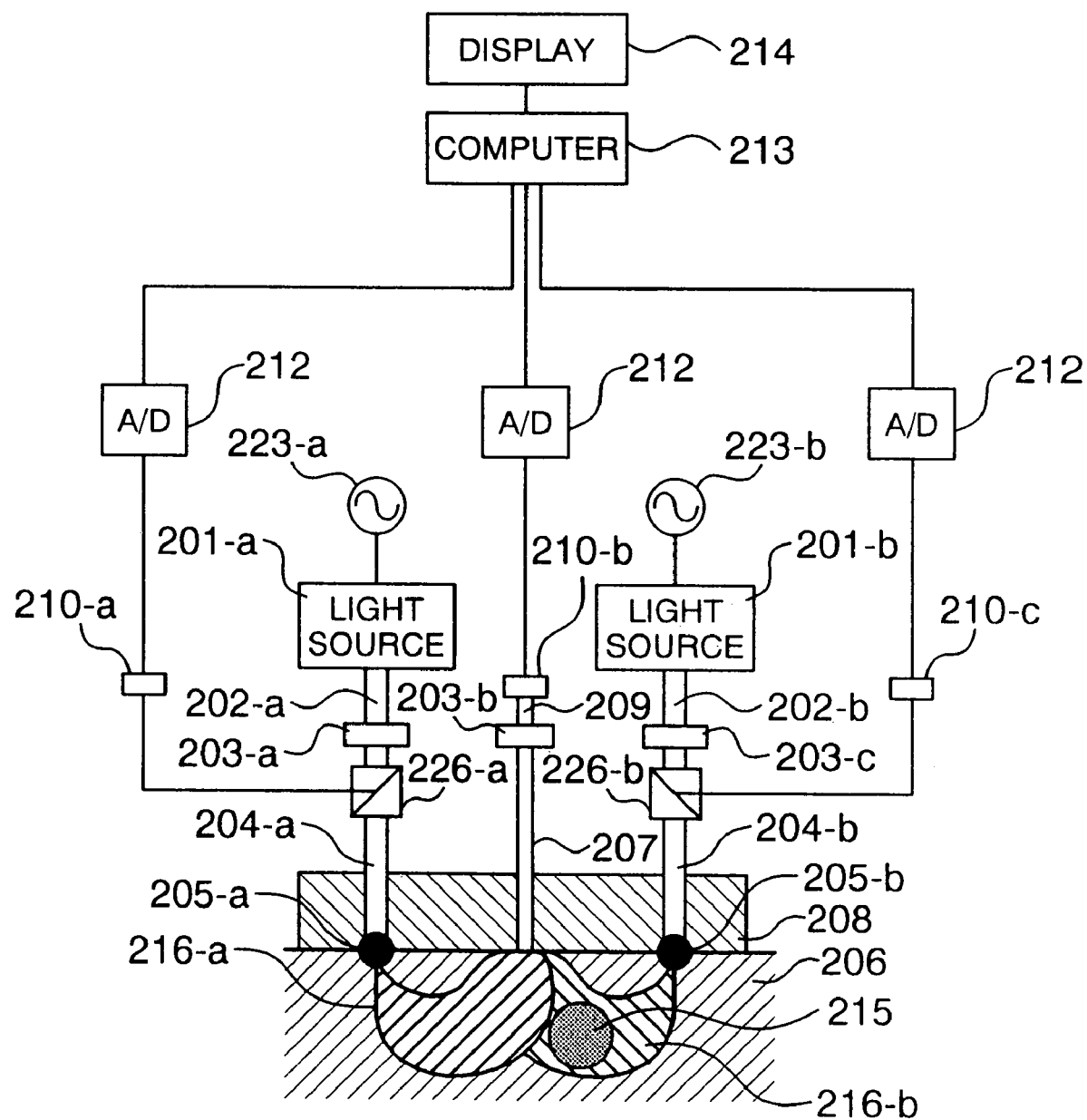
FIG. 23 is a block for explaining the construction of a system according to another embodiment of the present invention.

Alternatively, as shown in FIG. 23, the lock-in amplifiers, logarithmic amplifiers and differential amplifiers may not be used, detection signals from the photodetectors 210a, 210b and 210c may be converted into digital signals by the A/D converters 212, respectively, the digital signals may then be FFT processed with the computer 213 to extract only signals corresponding to intensity modulation frequencies of the respective light sources, a relative change amount calculated and determined through a similar procedure to the above calculation process can be displayed graphically as time series data on the display unit 214.

In the present invention, since the low cost light irradiation means and photodetectors are used to realize the simplified arithmetic processing, the high-speed processing can be ensured with an economical system and the living body function in correspondence to a plane image illustrative of the shape of an object to be measured can be imaged, thus ensuring that means effective especially for measurement of the local function of living body can be provided.

According to the prior arts, when the hemodynamic movement of a subject is measured by alternately repeating unloading and loading, the reference value varies and correct measurement cannot be carried out unless the measurement is delayed until signals to be measured are stabilized by keeping the subject quiet. According to the measuring method of the present invention, measurement can be conducted without waiting for the stabilization of signals. Further, measured signals can be removed of fluctuation to promote accuracy of signals.

When the first and second detection positions are set at locations which are substantially equidistant from the light irradiation position, transmitting light intensity signals at the respective detection positions equally change with an overall change in hemodynamic movement in a living body. Accordingly, by taking a logarithmic difference between a transmitting light intensity signal at the first detection position and a transmitting light intensity signal at the second detection position, a signal change attributable to the overall hemodynamic movement change can be removed. Further, when a change attributable to local hemodynamic movement is included in only one of transmitting light intensity signals at the first and second detection positions, the transmitting light intensity logarithmic difference signal reflects only the local change in hemodynamic movement.

The light ray comes into the living body through the light irradiation position and passes through complicated paths while interacting with various tissues of the living body and undergoing scattering and attenuation before it goes out of the living body through the light detection position. In the present invention, since the logarithmic difference between light intensity levels going out of the living body through positions which are substantially equidistant from the light irradiation position, the influence of scattering and attenuation caused by the tissues of the living body can be cancelled out and a slight signal reflecting the local change in hemodynamic movement can be detected with high accuracy.

Concretely, when an operation for cutting off a portion of the cerebrum is conducted in determination of the focus of epilepsy and therapy of serious epilepsy, an image of the portion to be cut off can be used to confirm that the cutting-off portion is a portion which does not impair the important in vivo function of the subject.

The invention claimed is:

1. An optical system for measuring change in cerebral hemodynamic movement comprising:
    a plurality of light irradiators for irradiating light rays on a head portion of a subject;
    a plurality of light receivers for receiving light rays reflected within said subject;
    a computing unit for calculating spatial distribution of signals of an object to be measured on the basis of signals detected by said light receivers; and
    a display unit for displaying said spatial distribution;
    wherein plural said light receivers adjacent to a common said light irradiator, are all disposed on positions distant by a substantially same distance from said common said light irradiator, where said distance is not less than 10 mm and not larger than 50 mm.

2. An optical system for measuring change in cerebral hemodynamic movement comprising:
    a plurality of light irradiators for irradiating light rays on a head portion of a subject;
    a plurality of light receivers for receiving light rays reflected within said subject;
    a computing unit for calculating spatial distribution of signals of an object to be measured on the basis of signals detected by said light receivers; and
    a display unit for displaying said spatial distribution;
    wherein plural said light receivers adjacent to a common said light irradiator, are all disposed on positions distant by a substantially same distance from said common said light irradiator, where said distance is not less than 10 mm and not larger than 50 mm;
    wherein one of said light receivers detect light rays irradiated by some of said light irradiators adjacent to said one of said light receivers; and
    wherein light rays irradiated by said one of said light irradiators are detected by said some of said light receivers adjacent to said one of said light irradiators.

3. An optical system for measuring change in cerebral hemodynamic movement comprising:
    a plurality of light irradiators for irradiating light rays on a head portion of a subject;

a plurality of light receivers for receiving light rays reflected within said subject;

a computing unit for calculating spatial distribution of signals of an object to be measured on the basis of signals detected by said light receivers; and a display unit for displaying said spatial distribution;

wherein said plurality of light irradiators and said plurality of light receivers are alternately arranged on said head portion of said subject in lattice; and wherein plural said light receivers adjacent to a common said light irradiator, are all disposed on positions distant by a substantially same distance from said common said light irradiator, where said distance is not less than 10 mm and not larger than 50 mm.

4. An optical system according to claim 1,
wherein said display unit displays the signals of said object in order of measuring time or as a dynamic image.

5. An optical system according to claim 1, further comprising:

a modulator for modulating light rays irradiated by said light irradiators in intensity with desired frequencies; and a separator for separating the light rays modulated by said modulator every modulation frequency.

6. An optical system according to claim 5,
wherein said modulator modulates the light rays with different frequencies in intensity at individual positions of said light irradiators.

7. An optical system according to claim 1,
wherein said light irradiators irradiate a plurality of light rays whose wavelengths are different from each other.

8. An optical system according to claim 7,
wherein the number of wavelengths of light rays irradiated from said light irradiators is equal to a number of absorbers of said object to be measured.

9. An optical system according to claim 7, further comprising:

a modulator in which the light rays irradiated by said light irradiators are modulated in intensity with different modulation frequencies at individual wavelengths of said light rays; and a separator for separating the light rays modulated by said modulator every modulation frequency.

10. An optical system according to claim 5,
wherein said separator is composed of lock-in amplifiers which are operated on the basis of the modulation signals of said modulator.

11. An optical system according to claim 1,
wherein the signals of the object are relative change amounts of concentration of hemoglobin oxide or reduced hemoglobin.

12. An optical system according to claim 1,
wherein said display unit displays the signal of the object as time integral values or a time-average values of relative change amounts of concentration of hemoglobin oxide or reduced hemoglobin.

13. An optical system according to claim 1,
wherein said display unit displays the signal of the object as a distribution representative of a change in hemodynamic movement attributable to a cerebral function of said subject.

14. An optical system according to claim 1,
wherein said display unit displays the signal of the object by a contour map, a light and shade image of a color or a discrimination display in color.

15. An optical system according to claim 1,
wherein the light rays irradiated by said light irradiators are light rays having a wavelength in a region from visible rays to near infrared rays.

16. An optical system according to claim 1,
wherein measuring points are on intermediate positions between said light irradiators and said light receivers;

wherein said computing unit calculates interpolation signals of the objection at positions between the said measuring points on the basis of the signals of the object at the measuring points, and wherein said display unit displays the interpolation signals.

17. An optical system according to claim 1,
wherein said display unit displays the signals of the object to be measured by superimposing said signals on a cerebral image of the object to be measured.

18. An optical system according to claim 17, wherein said cerebral image is an image of the form of three-dimensional MRI or three-dimensional X-ray CT.

19. An optical system according to claim 1, wherein said light irradiators includes light sources whose the irradiating light rays have wavelengths different from each other, and waveguides for guiding the light rays from said light sources to the irradiating positions.

20. An optical system according to claim 1, wherein measuring points are on intermediate positions between said light irradiators and said light receivers; and wherein said computing unit calculates a mutual correlation function between time-variable changes of signal intensity of said object to be measured at first one of said measuring points and time-variable changes of signal intensity of said object to be measured at second one of said measuring points.

* * * * *